US012806282B2

(12) United States Patent
Kim et al.

(10) Patent No.: US 12,806,282 B2
(45) Date of Patent: Nov. 24, 2026

(54) RECOMBINANT EXOSOME AND USE THEREOF

(71) Applicants: KOREA INSTITUTE OF SCIENCE AND TECHNOLOGY, Seoul (KR); REONEBIO, Seoul (KR)

(72) Inventors: In-San Kim, Seoul (KR); Gi-Hoon Nam, Seoul (KR); Yeon-Sun Hong, Seoul (KR); Seong Eon Cho, Seoul (KR)

(73) Assignees: KOREA INSTITUTE OF SCIENCE AND TECHNOLOGY, Seoul (KR); REONEBIO, Seoul (KR)

( * ) Notice: Subject to any disclaimer, the term of this patent is extended or adjusted under 35 U.S.C. 154(b) by 1010 days.

(21) Appl. No.: 17/937,437

(22) Filed: Sep. 30, 2022

(65) Prior Publication Data

US 2023/0226215 A1 Jul. 20, 2023

Related U.S. Application Data

(63) Continuation of application No. PCT/KR2021/003701, filed on Mar. 25, 2021.

(30) Foreign Application Priority Data

Apr. 10, 2020 (KR) ........................ 10-2020-0043869

(51) Int. Cl.

*A61K 47/69* (2017.01)
*A61K 9/06* (2006.01)
*A61K 35/28* (2015.01)
*A61K 38/17* (2006.01)
*A61K 38/18* (2006.01)
*A61P 17/02* (2006.01)

(52) U.S. Cl.

CPC ............ *A61K 47/6911* (2017.08); *A61K 9/06* (2013.01); *A61K 35/28* (2013.01); *A61K 38/177* (2013.01); *A61K 38/1774* (2013.01); *A61K 38/179* (2013.01); *A61K 38/1796* (2013.01); *A61K 38/1808* (2013.01); *A61P 17/02* (2018.01)

(58) Field of Classification Search

None

See application file for complete search history.

(56) References Cited

PUBLICATIONS

Castellanos et al., Placenta, vol. 59, Nov. 2017, pp. 146-153 (Year: 2017).*
Ohno et al., Molecular Therapy vol. 21, No. 1, Jan. 2013, pp. 185-191 (Year: 2013).*
Nedawi et al., Nature Cell Biology, vol. 10, No. 5, May 2008, pp. 619-624 (Year: 2008).*
Wu et al., Molecular Cancer (2021) 20:17, 17 pages (Year: 2021).*
Zhang et al., Nature Communications, 8:15016, 11 pages, published Apr. 10, 2017 (Year: 2017).*

* cited by examiner

*Primary Examiner* — Evelyn Y Pyla

(74) *Attorney, Agent, or Firm* — United One Law Group LLC; Kongsik Kim; Jhongwoo Peck

(57) ABSTRACT

The present invention provides a recombinant exosome comprising a membrane-bound EGF protein on the surface of the recombinant exosome and provides a use of the recombinant exosome.

18 Claims, 26 Drawing Sheets

Specification includes a Sequence Listing.

RECOMBINANT EXOSOME AND USE THEREOF

CROSS-REFERENCE TO RELATED APPLICATIONS

This application is a continuation of International Application No. PCT/KR2021/003701 filed on Mar. 25, 2021, which claims priority to Korean Application No. 10-2020-0043869 filed on Apr. 10, 2020. The applications are incorporated herein by reference.

REFERENCE TO ELECTRONIC SEQUENCE LISTING

The application contains a Sequence Listing which has been submitted electronically in .XML format and is hereby incorporated by reference in its entirety. Said .XML copy, created on Mar. 28, 2023, is named "SFT-P30005C.xml" and is 13,872 bytes in size. The sequence listing contained in this .XML file is part of the specification and is hereby incorporated by reference herein in its entirety.

TECHNICAL FIELD

The present invention relates to novel recombinant exosomes and their uses, more specifically to recombinant exosomes with recombinant epidermal growth factors (EGFs) displayed on the membranes of the recombinant exosomes and to uses of the recombinant exosomes.

BACKGROUND ART

Human EGF is a type of growth factor consisting of 53 amino acids, having a size of 6 kDa, and having three intramolecular disulfide bonds. EGF binds to a receptor, EGFR (a type of receptor tyrosine kinase) and induces dimerization of EGFR, thereby activating the protein tyrosine kinase pathway in the cytoplasm and eventually playing a role in cell proliferation, and EGF also sometimes participates in cell differentiation and survival. Recombinant human EGF is marketed under the trade name Hebroprot-P as a therapeutic agent for treating diabetic foot ulcers, and it is known that EGF can be used as a therapeutic agent for healing wound on the skin or cornea and as a therapeutic agent for treating gastric ulcers (U.S. Pat. No. 6,656,907; Carpenter and Zendegui, *Exp. Cell Res.,* 164: 1-10, 1986). In addition, in recent years, it has been used for rapid implantation of biografts into tissues and rapid repair of defects of biografts by being attached to the surface of synthetic scaffolds that are used to manufacture various bioimplants (Goodarzi et al., *Adv. Exp. Med. Biol.,* 1107: 143-188, 2018; Haddad et al., *Biomatter,* 6(1): e1231276, 2015). However, there is a problem that the effect of wound healing is very low when EGF is applied to an actual wound site, while the effect of promoting epithelial cell differentiation is excellent when it is applied in vitro, and it has been difficult to use EGF to develop a therapeutic agent for treating wound on the skin or cornea. The reason why the wound healing effect is not sufficiently shown when EGF is directly applied to the living body is that because EGF is not only biologically unstable but also physicochemically inhomogeneous, the therapeutic effect is low and its degradation products cause allergies. In more detail, EGF is very unstable at room temperature, especially in the presence of moisture; while about 8 to 12 hours (lag time) are required to induce cells to synthesize DNA at a wound site, the half-life of EGF is so short (about 1 hour) that EGF cannot exhibit the desired would healing effect; since EGF is a pure polypeptide, physicochemical changes occur during long-term storage not only at room temperature but also even in a refrigerated state; and EGF, when it is applied to the skin, may be denatured by proteolytic enzymes present in the wound site, dissociated, agglomerated, and precipitated, thereby causing EGF to lose its biological activity (see Manning et al., *Pharm. Res.,* 6: 903-917, 1989).

On the other hand, EGF is known as a secretory protein, but it undergoes a secretion route different from a typical secretion route. That is, EGF is synthesized in the form of a membrane protein, it travels to the cell membrane through the ER pathway, and it is secreted outside the cell after cleavage occurs at the internal cleavage site. Thus, a mature water-soluble protein of 53 a.a. has been of interest as a potential therapeutic agent, and the whole length protein or the form of EGF presented in the membrane has been of no interest.

On the other hand, exosomes are known to be small vesicles that are composed of double lipid layer membranes (cell membranes), are secreted by eukaryotic cells such as animals and plants, perform specialized functions such as coagulation, cell-to-cell signaling, and cell "waste management," and are secreted out to body fluids by forming disease-specific nucleic acids and proteins. Because exosomes are relatively safe in that they have membrane structures surrounded by cell membrane components secreted from cells, and because they can load various bioactive substances such as proteins, nucleic acids, or compounds inside the exosomes or on the surface of the exosomes, exosomes have been, recently, used as a drug itself or as a drug delivery system carrying other drugs and delivering them to a target of interest.

The prior art technology includes Korean Patent Application Publication No. 2018-0005546 directed to a drug-loaded exosome and Korean Patent Application Publication No. 2018-0078173 directed to a recombinant exosome in which a phagocytic promoting protein is presented on the surface of the exosome and a use thereof.

However, there have been only some attempts to improve the stability of the preparation including EGF by replacing excipients or the like, and any technology has not been proposed to provide EGF in a form suitable for actual wound treatment.

Accordingly, as a solution to various problems including the above-described problems, the present invention provides a new type of EGF platform in which wound healing ability is significantly increased compared to a recombinant EGF itself. However, this is only an example of the present invention, and the scope of the present invention should not be limited thereto.

SUMMARY

According to an aspect of the present invention, a recombinant exosome containing a membrane-bound EGF protein on the surface of the recombinant exosome.

According to another aspect of the invention, the present invention provides a pharmaceutical composition for treating wound, which comprises the recombinant exosome as an active ingredient.

According to another aspect of the invention, the present invention provides a pharmaceutical composition for treating ulcer, which comprises the recombinant exosome as an active ingredient.

According to another aspect of the present invention, the present invention provides a pharmaceutical composition for treating burns, which comprises the recombinant exosome as an active ingredient.

According to another aspect of the present invention, the present invention provides a pharmaceutical composition for improving skin aging, which comprises the recombinant exosome as an active ingredient.

According to another aspect of the present invention, the present invention provides a pharmaceutical composition for treating keloid skin, which comprises the recombinant exosome as an active ingredient.

According to another aspect of the present invention, the present invention provides a pharmaceutical composition for treating diabetic foot lesions (DM foot), which comprises the recombinant exosome as an active ingredient.

According to another aspect of the present invention, the present invention provides a pharmaceutical composition for treating dermatitis, which comprises the recombinant exosome as an active ingredient.

According to another aspect of the present invention, the present invention provides a pharmaceutical composition for treating rosacea, which comprises the recombinant exosome as an active ingredient.

According to another aspect of the present invention, the present invention provides a pharmaceutical composition for treating atopic diseases, which comprises the recombinant exosome as an active ingredient.

According to another aspect of the present invention, the present invention provides a pharmaceutical composition for treating psoriasis, which comprises the recombinant exosome as an active ingredient.

According to another aspect of the present invention, the present invention provides a pharmaceutical composition for treating eczema, which comprises the recombinant exosome as an active ingredient.

According to another aspect of the present invention, the present invention provides a pharmaceutical composition for treating scar, which comprises the recombinant exosome as an active ingredient.

According to another aspect of the present invention, the present invention provides a pharmaceutical composition for treating acne, which comprises the recombinant exosome as an active ingredient.

According to another aspect of the present invention, the present invention provides a functional cosmetic composition for regenerating skin, which comprises the recombinant exosome as an active ingredient.

According to another aspect of the present invention, the present invention provides a method of treating wound or ulcer of a subject, which comprises administering a therapeutically effective amount of the recombinant exosome to the subject having wound or ulcer.

According to another aspect of the invention, the present invention provides a use of the recombinant exosome for preparation of a therapeutic pharmaceutical composition of treating symptoms requiring epithelial cell proliferation.

According to another aspect of the present invention, the present invention provides a use of the recombinant exosome for preparation of a cosmetic composition for regenerating skin, reducing skin aging, or improving wrinkles.

According to an embodiment of the present invention, compared to conventional recombinant EGFs, a pharmaceutical composition having a highly stable and effective ability to proliferate epithelial cells and a highly stable and effective ability to heal wounds is provided. Of course, the scope of the present invention should not be limited thereto.

DETAILED DESCRIPTION

Definitions

Figure 1A:
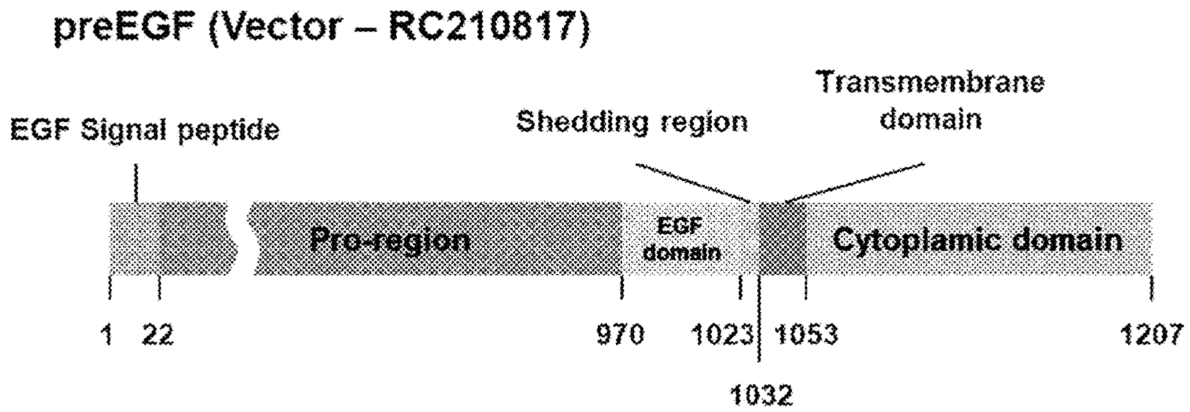
FIG. 1A is a schematic diagram illustrating the structure of a full-length EGF protein (preEGF) used in the preparation of a recombinant exosome (preEGF-Exo) according to an embodiment of the present invention. The number at the bottom shows the amino acid location.

As used herein, the term "exosome" is a small vesicle that is composed of double lipid layer membranes, is secreted by eukaryotic cells, performs specialized functions such as coagulation, cell-to-cell signaling, and cell "waste management," and is secreted out to body fluids by forming disease-specific nucleic acids and proteins.

The term "recombinant exosome" used herein is the opposite of a naturally occurring exosome, and it refers to an exosome that is produced in a host cell transformed to produce a foreign protein expressed by a foreign gene by transfecting the foreign gene into the host cell.

The term "epidermal growth factor" (EGF) used herein refers to a protein that binds to a receptor, EGFR (a type of receptor tyrosine kinase) and induces dimerization of EGFR, thereby activating the protein tyrosine kinase pathway in the cytoplasm and eventually playing a role in cell proliferation, and sometimes also participating in cell differentiation and survival.

As used herein, the term "mature EGF" is a secretory EGF that has a molecular weight of 6 kDa, has three disulfide bonds in the molecule consisting of 53 a.a., and does not have any prePro peptide, any transmembrane domain, and any cytoplasmic domain portion. "Mature EGF" may also be called "free EGF" or "secretory EGF" because it is typically secreted extracellularly.

As used herein, the term "membrane-bound EGF" or "membrane surface displayed EGF" refers to a form of EGF protein that is bound to a membrane or displayed on the surface of a membrane as the mature EGF is coupled to a transmembrane domain of the original EGF or a transmembrane domain derived from another transmembrane protein. That is, the term "membrane-bound EGF" or "membrane surface displayed EGF" used herein can be regarded as the opposite concept of "free EGF" or "secretory EGF" that circulates the blood. Here, the full-length EGF, which comprises not only the mature EGF and but also the transmembrane domain of the original EGF, is named a "wild-type EGF (wtEGF)" or a "precursor EGF (preEGF)." Optionally, EGF may be bound to a membrane or displayed on the surface of a membrane by using a GPI-anchor instead of the transmembrane domain.

As used herein, the term "transmembrane domain" refers to a site of a cell membrane that is responsible for fixing a protein to the cell membrane. Typically, transmembrane domains are present in various types of transmembrane proteins. The transmembrane proteins include various transporters, ion channels, GPCRs, receptor tyrosine kinases (RTK), T cell receptors, clusters of differentiation, and the like. The transmembrane domains include a single-pass domain present in the RTK or a 7-pass domain present in the GPCR. The single-pass protein is classified into types 1 to 4 depending on it topology, i.e. whether the N-terminus is present in the cytoplasm or outside the cell. Specifically, the type 1 transmembrane protein has the N-terminal outside the cell and has the cytoplasmic domain part in the cytoplasm. The type 2 transmembrane protein, on the contrary, has the C-terminal outside the cell and the N-terminal part in the cytoplasm. The type 3 and type 4 transmembrane proteins are a kind of anchor proteins. The type 3 transmembrane protein has the C-terminal forming an extracellular domain and the N-terminus being adjacent to the cell membrane and not forming a particular domain. The type 4 transmembrane protein has the C-terminal that is present outside the cytoplasm and does not form an extracellular domain because the terminal is adjacent to the cell membrane, while the N-terminal forms the cytoplasmic domain. Therefore, in order to display EGF outside the cell, it is preferable to use the transmembrane domain of the type 1 transmembrane protein. Examples of the transmembrane domain of the type 1 transmembrane protein may include transmembrane domains of RKT, transmembrane domains of immune receptors (TCR, beta or zeta chains), transmembrane domains (such as CD28, CD3ε, CD45, CD4, CD5, CD8, CD9, CD16, CD22, CD33, CD37, CD64, CD80, CD86, CD134, CD137, and CD154) of various clusters of differentiation.

As used herein, the term "immune receptor" refers to a receptor that binds to a specific substance (e.g., an antigen) and causes a response of the immune system. Examples of the immune receptor may include pattern recognition receptors (PRRs), killer activated receptors (TAR), killer inhibitor receptors (KIR), complement receptors, Fc receptors, B cell receptors, T cell receptors, and cytokine receptors.

According to an aspect of the present invention, a recombinant exosome comprising a membrane-bound EGF protein on the surface of the exosome is provided.

The membrane-bound EGF protein may include a transmembrane domain. The EGF protein may further include a cytoplasmic domain. Optionally, the membrane-bound EGF protein may be fixed to the membrane by a GPI-anchor.

The transmembrane domain may be a transmembrane domain of a full-length EGF protein or a transmembrane domain derived from another transmembrane protein.

The transmembrane protein may be a receptor protein, an ion channel, a transporter, a cluster of differentiation (CD), or a membrane-bound enzyme.

The receptor protein may be a receptor tyrosine kinase (RTK), an immune receptor, or a G protein-coupling receptor (GPCR).

The RTK may include a platelent-derived growth factor receptor (PDGFR), an epidermal growth factor receptor (EGFR), a fibroblast growth factor receptor (FGFR), a vascular endothelial growth factor receptor (VEGFR), a hepatocyte growth factor receptor (HGFR), tropomyosin receptor kinase (Trk), an insulin receptor (IR), a Leukocyte receptor tyrosine kinase (LTK), an angiopoietin receptor, a receptor tyrosine kinase-like orphan receptor (ROR), a discoidin domain receptor (DDR), a rearranged during transfection receptor (RETR), a tyrosine-protein kinase-like (PTK), a receptor tyrosine kinase-related molecule (RYK), or a muscle-specific kinase (MuSK). The RTK may be any one other than PDGFR.

The GPCR may be an alpha receptor, a beta receptor, a chemokine receptor, a dopamine receptor, a histamine receptor, an opioid receptor, a nociceptin receptor, a sphingosine-1-phosphate receptor, an opsin, or rhodopsin.

The CD may be CD28, CD3ε, CD45, CD4, CD5, CD8, CD9, CD16, CD22, CD33, CD37, CD64, CD80, CD86, CD134, CD137, or CD154.

The immune receptor may be a pattern recognition receptor (PRR), a killer activated receptor (TAR), a killer inhibitor receptor (KIR), a complement receptor, an Fc receptor, a B cell receptor, a T cell receptor, or a cytokine receptor.

The recombinant exosome may be isolated from a protein production cell line or a mesenchymal stem cell. The protein production cell line may be CHO, HKB11, BHK21, HeLa, HEK293, HT-1080, PER.C6, or F2N78. The CHO cell line may be a CHO DHFR$^-$ cell line, and the CHO DHFR$^-$ cell line may be a CHO DXB11 or CHO DG44 cell line.

According to another aspect of the invention, there is provided a pharmaceutical composition for treating wound, which comprises a therapeutically effective amount of the recombinant exosome and a pharmaceutically acceptable carrier.

According to another aspect of the invention, there is provided a pharmaceutical composition for treating ulcer, which comprises a therapeutically effective amount of the recombinant exosome and a pharmaceutically acceptable carrier.

The ulcer may be gastric ulcer, lower limb ulcer, skin ulcer, genital ulcer, mouth ulcer, esophageal ulcer, bladder ulcer, gallbladder ulcer, foot ulcer, duodenal ulcer, gastric ulcer, or colon ulcer.

According to another aspect of the invention, there is provided a pharmaceutical composition for treating burns, which comprises a therapeutically effective amount of the recombinant exosome and a pharmaceutically acceptable carrier.

A number of studies have reported that EGF shortened treatment time for second-degree burns and significantly lowered scar index (Bi et al., *Int. J. Clin. Med.* 10(7): 9871-9876, 2017). Thus, the recombinant exosomes of the present invention can be effectively used for the treatment of burns.

According to another aspect of the invention, there is provided a pharmaceutical composition for improving skin aging, which comprises the recombinant exosome as an active ingredient.

EGF has also been reported to exhibit a regenerative effect on aging skin by improving the migration and contraction of aged fibroblasts (Kim et al., *Int. J. Mol. Med.* 35(4): 1017-1025, 2015). Therefore, the recombinant exosomes of the present invention can be used as active ingredients of pharmaceutical compositions or cosmetic compositions for the improvement of aged skin.

According to another aspect of the present invention, there is provided a pharmaceutical composition for treating keloid skin, which comprises the recombinant exosome as an active ingredient.

Keloid skin refers to skin swollen by stimulus including scratches. Recent studies have reported that EGF prevented keloid skin from reoccurring (Joseph et al., *Int. Surg. J.* 6(9): 3341-3346, 2019). Thus, the recombinant exosome according to an embodiment of the present invention can be used for treating and preventing keloid skin.

According to another aspect of the invention, there is provided a pharmaceutical composition for treating diabetic foot lesions (DM foot), which comprises the recombinant exosome as an active ingredient.

A number of studies have reported that EGF was effective in the treatment of diabetic foot ulcers (Bui et al., *Int. J. Environ. Res. Public Health,* 16(14): 2584, 2019). Thus, recombinant exosomes according to one embodiment of the present invention can be used for the treatment of diabetic foot lesions, including diabetic foot ulcers.

According to another aspect of the present invention, there is provided a pharmaceutical composition for treating dermatitis, which comprises the recombinant exosome as an active ingredient.

It was reported that EGF, when it was topically administered to the skin, improved the inflammatory response of the skin (Kim et al., *Sci. Rep.,* 8: 11895, 2018) and improved symptoms of atopic dermatitis (Choi et al., *BioMed Res. Int. Article ID* 9439182, 2018). Therefore, the recombinant exosomes according to an embodiment of the present invention can be effectively used for the treatment of dermatitis or atopic diseases.

According to another aspect of the present invention, there is provided a pharmaceutical composition for treating rosacea, which comprises the recombinant exosome as an active ingredient.

According to another aspect of the present invention, there is provided a pharmaceutical composition for treating atopic diseases, which comprises the recombinant exosome as an active ingredient.

U.S. Patent Application Publication No. US20080317727A discloses a method of treating rosacea by using EGF. Thus, the recombinant exosomes according to an embodiment of the present invention can be effectively used for the treatment of rosacea.

According to another aspect of the present invention, there is provided a pharmaceutical composition for treating psoriasis, which comprises the recombinant exosome as an active ingredient.

According to another aspect of the present invention, there is provided a pharmaceutical composition for the treating eczema, which comprises the recombinant exosome as an active ingredient.

According to another aspect of the present invention, there is provided a pharmaceutical composition for treating scars, which comprises the recombinant exosome as an active ingredient.

According to another aspect of the present invention, there is provided a pharmaceutical composition for treating acne, which comprises the recombinant exosome as an active ingredient.

According to another aspect of the present invention, there is provided a functional cosmetic composition for regenerating skin, which comprises the recombinant exosome as an active ingredient.

Cosmetic compositions according to an aspect of the present invention may include functional cosmetics, face washes, and shampoos, for example. Formulations of the cosmetic compositions according to an embodiment of the present invention include, for example, lotions, creams, essences, nutritional water, cosmetic liquid and packs, soaps, shampoos, conditioners, cleansing, body cleansers, face washes, treatments, and cosmetic water.

The cosmetic compositions of the present invention may further comprise one or more additional functional component selected from the group consisting of water-soluble vitamins, fat-soluble vitamins, polymer peptides, polymer polysaccharides, sphingolipids, and seaweed extracts.

As a water-soluble vitamin, anything that can be contained in a cosmetic composition may be used. Examples of the water-soluble vitamin may include vitamin B1, vitamin B2, vitamin B6, pyridoxine, pyridoxine hydrochloride, vitamin B12, pantothenic acid, nicotinic acid, nicotinic acid, folic acid, vitamin C, vitamin H, and the like, as well as their salts (thiamine hydrochloride, sodium ascorbate salt, etc.) or derivatives (ascorbic acid-2-phosphate sodium salt, ascorbic acid-2-phosphate magnesium salt, etc.). The water-soluble vitamins can be obtained by conventional methods such as microbial conversion methods, purification methods from cultures of microorganisms, enzymatic methods or chemical synthesis methods.

As a fat-soluble vitamin, anything that can be contained in a cosmetic composition may be used. Examples of the fat-soluble vitamin may include vitamin A, carotene, vitamin D2, vitamin D3, vitamin E (dl-α-tocopherol, d-α-tocopherol, d-δ-tocopherol), and their derivatives (ascorbin palmitate, ascorbin stearate, ascorbin dipalmitate, dl-α-tocopherol acetate, dl-α-tocopherol nicotinic acid, DL-pantothenyl alcohol, D-pantothenyl alcohol, pantothenylethyl ether, etc.).

The fat-soluble vitamins can be obtained by conventional methods such as microbial conversion methods, purification methods from cultures of microorganisms, enzymatic or chemical synthesis methods, etc.

As a polymer peptide, anything that can be contained in a cosmetic composition may be used. Examples of the polymer peptide may include collagen, hydrolyzed collagen, gelatin, elastin, hydrolyzed elastin, keratin, and the like. The polymer peptide can be purified and obtained by conventional methods such as purification method, enzymatic method or chemical synthesis method from the culture medium of microorganisms, or it can be purified and used from natural products such as dermis of pigs or cattle, fibers of silkworms, or the like.

As a polymer polysaccharide, anything that can be contained in a cosmetic composition may be used. Examples of the polymer polysaccharide may include hydroxyethylcellulose, xanthan gum, sodium hyaluronate, chondroitin sulfate, and salts thereof (sodium salt, etc.). For example, chondroitin sulfate or salts thereof can be purified and used from ordinary mammals or fish.

As a sphingo lipid, anything that can be contained in a cosmetic composition may be used. Examples of the sphingo lipid may include ceramide, pit sphingosine, sphingosaccharide lipids, and the like. The sphingo lipids can be purified by conventional methods from mammals, fish, shellfish, yeast or plants, or obtained by chemical synthesis methods.

As a seaweed extract, anything that can be contained in a cosmetic composition may be used. Examples of the seaweed extract may include goldenrod extract, flush extract, green algae extract, and the like. Also, callaginan, arginate, sodium arginate, potassium arginate, etc. purified from their seaweed extract may also be used. The seaweed extract can be obtained by purifying it by conventional methods from seaweed.

In the cosmetic composition of the present invention, in addition to the essential ingredients, other components that are typically added may be added, as desired.

Other additional components that may be added may include oils and fats, moisturizers, emolients, surfactants, organic and inorganic pigments, organic powders, ultraviolet absorbers, preservatives, disinfectants, antioxidants, plant extracts, pH adjusters, alcohols, colors, fragrances, blood circulation promoters, cooling agents, limiting agents, purified water, and the like.

As oils and fats, ester oil, hydrocarbon oil, silicon oil, fluorine oil, animal oil, plant oil, and the like may be used. Examples of the ester oils and fats may include tri2-ethylhexanerate glyceryl ethylhexane, cetyl 2-ethylhexanoate, isopropyl myristicate, butyl myristic, isopropyl palmitate, ethyl stearate, octyl palmitate, isocetyl isostearate, butyl stearate, ethyl linoleate, isopropyl linoleate, ethyl oleinate, isocetyl myristinate, isostearyl myristinate, isostearyl palmitate, octyldodecyl myristic, isocetyl isostearate, diethyl sebacinate, diisopropyl adipinate, neopencarbonate isoalkyl, tri(caprylic, capric acid) gliceryl, tri2-trimethylolpropane ethylhexanerate, trimethylrolpropane triisostearate, tetra-2-ethylhexane pentaelislitol, cetyl caprylate, decyl laurate, hexyl laurate, decyl myristinate, myristic acid decyl, myristic acid myristyl myristate, stearyl stearate, decyl oleinate, cetyl lisinooleate, isostearyl laurate, isotridecyl myristicate, isocetyl palmitate, octyl stearate, isocetyl stearate, isodecyl oleinate, octyldodecyl oleinate, octyldodecyl linoleate, isopropyl isostearate, 2-ethylhexanate cetostearyl, 2-ethylhexane stearyl, isostearic acid hexyl, ethylene dioctanoic acid, ethylene glycol dioleate, propylene dicapriclate glycol, di(caprylic/capric acid) propylene glycol, propylene glycol dicaprylate, neopentyl dicapriclate dicapricane, dioctanoneopentyl glycol, glyceryl tricaprylate, glyceryl triundecyl acid, glyceryl triisopalmitate, glyceryl triisostearate, octyldodecyl neopencarbonate, isostearyl octanoate, octyl isononanoate, hexyldecyl neodecanoate, octyldodecyl neodecanoate, octyldodecyl neoccanate, isocetyl isostearate, isostearyl isostearate, octyldecyl isostearate, polyglycerin oleic acid ester, polyglycerin isostearate ester, triisocetyl citrate, triisoalkyl citrate, triisooctyl citrate, lauryl lactate, myristyl lactate, cetyl lactate, octyldecyl lactate, triethyl citrate, acetyl citrate, acetyl tributyl citrate, trioctyl malate, diisostearyl malate, hydroxystearate 2-ethylhexyl, di-2-ethylhexyl succinate, diisobutyl adipinate, diisopropyl sebacinate, dioctyl sebacinate, cholesteryl stearate, cholesteryl isostearate, cholesteryl hydroxystearate, cholesteryl oleate, dihydrocholesteryl oleate, pitesteryl isostearate, pitesteryl oleinate, isosteyl hydroxystearate, isocetyl 12-stealoyl hydroxystearate, isostearyl isostearyl 12-stealoyl hydroxystearate, and the like.

Examples of the hydrocarbon-based oils and fats may include squalene, flow paraffin, α-olefin oligomers, isoparaffin, ceresin, paraffin, flow isoparaffin, polybudene, microcrystalline wax, vaseline, and the like.

Examples of the silicone oils and fats may include polymethylsilane, methylphenylsilane, methylcyclopolysiloxane, octamethylpolysiloxane, decamethylpolysiloxane, dodecamethylcyclosiloxane, dimethylsiloxane, methylcetyloxysiloxane copolymer, dimethylsiloxane, methylstealoxysiloxane copolymer, alkyl modified silicone oil, amino modified silicone oil, and the like.

An example of the fluorine oils is perfluoropolyetherz.

Examples of the animal or plant oils may include avocado oil, armmond oil, olive oil, sesame oil, rice bran oil, sour flower oil, soybean oil, corn oil, rapeseed oil, apricot oil, palm kernel oil, palm oil, castor oil, sunflower oil, grape seed oil, cottonseed oil, palm oil, cucui nut oil, wheat germ oil, rice germ oil, shea butter, moonshine colostrum oil, marker damia nut oil, meadow home oil, egg yolk oil, tallow, horse oil, mink oil, orange lapee oil, jojoba oil, cander wax, carnaba wax, liquid lanolin, and hydrogenated castor oil.

Examples of the moisturizer may include a water-soluble small molecule moisturizer, a fat-soluble molecular moisturizer, a water-soluble polymer, a fat-soluble polymer, and the like.

Examples of the water-soluble small molecule moisturizer may include serine, glutamine, sorbitol, mannitol, pyrrolidone-sodium carboxylate, glycerin, propylene glycol, 1,3-butylene glycol, ethylene glycol, polyethylene glycol (polymerization degree n=2 or more), polypropylene glycol (polymerization degree n=2 or more), polyglycerin (polymerization degree n=2 or more), lactic acid, lactate, and the like.

Examples of the fat-soluble small molecule moisturizer may include cholesterol and cholesterol esters.

Examples of the water-soluble polymers may include carboxyvinyl polymers, polyasparaginate, tragacanth, xanthan gum, methylcellulose, hydroxymethylcellulose, hydroxyethylcellulose, hydroxypropylcellulose, carboxymethylcellulose, water-soluble chitin, chitosan, dextrin, and the like. Fat-soluble polymers include polyvinylpyrrolidone, eicosen copolymers, polyvinylpyrrolidone, hexadecene copolymers, nitrocellulose, dextrin fatty acid esters, polymer silicones, and the like.

Examples of the emollients may include long-chain acyl glutamate cholesteryl esters, cholesteryl hydroxystearate, 12-hydroxystearic acid, stearic acid, rosin acid, lanolin fatty acid cholesteryl esters, and the like.

Examples of the surfactants may include nonionic surfactants, anionic surfactants, cationic surfactants, positive surfactants, and the like.

Examples of the nonionic surfactants may include self-emulsifying glycerin monostearate, propylene glycol fatty acid ester, glycerin fatty acid ester, polyglycerin fatty acid ester, sorbitan fatty acid ester, POE (polyoxyethylene) sorbitan fatty acid ester, POE sorbitan fatty acid ester, POE sorbitan fatty acid ester, POE alkyl ether, POE fatty acid ester, POE hydrogenated castor oil, POE castor oil, POE·POP (polyoxyethylene, polyoxypropylene) copolymer, POE·POP alkyl ether, polyether modified silicon, alcanolamide laurate, alkylamine oxide, hydrogenated soybean phospholipids, and the like.

Examples of the anionic surfactants may include fatty acid soaps, α-acylsulfonates, alkylsulfonates, alkyl allyl sulfonates, alkyl naphthalenesulfonates, alkyl sulfates, POE alkyl ether sulfates, alkylamide sulfates, alkyl phosphates, alkyl phosphates, alkyl acid phosphates, N-acyl amino acids, POE alkyl ethercarboxylates, alkyl sulfosuccinates, sodium alkyl sulfoacetate, acylated hydrolyzed collagen peptide salts, perfluoroalkyl phosphate esters, and the like.

Examples of the cationic surfactants may include alkyl trimethylammonium chloride, stearyl trimethylammonium chloride, stearyl trimethylammonium bromide, cetostearyltrimethylammonium chloride, distearyldimethylammonium chloride, stearyl dimethylbenzylammonium chloride, behenyltrimethylammonium bromide, benzalkonium chloride, diethylaminoethylamide stearate, dimethylaminopropylamide stearate, lanolin derivative grade 4 ammonium salt, and the like.

Examples of the positive surfactants may include positive surfactants such as carboxybeta dolls, amide beta dolls, sulfobeta dolls, hydroxysulfobeta dolls, amidesulfobeta dolls, phosphobeta dolls, aminocarboxylates, imidazoline derivative types, amide amine types, and the like.

Examples of the organic and inorganic pigments may include silicic acid, susilicic anhydride, magnesium silicate, talc, serisite, mica, kaolin, bengala, clay, bentonite, titanium coating mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine, chromium oxide, chromium hydroxide, calamine, carbon black and other inorganic pigments such as complexes thereof; Polyamide, polyester, polypropylene, polystyrene, polyurethane, vinyl resin, urea resin, phenolic resin, fluoroplastic, silicon resin, acrylic resin, melamine resin, epoxy resin, polycarbonate resin, divinylbenzene-styrene copolymer, silk powder, cellulose, CI pigment yellow, CI pigment orange, and other organic pigments and composite pigments of organic pigments thereof.

Examples of the organic powder may include metal soaps such as calcium stearate; Alkyl phosphate metal salts such as sodium zinc cetylate, zinc laurylate, calcium laurylite; Acyl amino acid polyhydric metal salts such as N-lauroyl-β-alanine calcium, N-lauroyl-β-alanine zinc, N-lauroyl glycine calcium; Amide sulfonic acid polyhydric metal salts such as N-lauroyl-taurine calcium, N-palmitoyl-taurine calcium and the like; N-acyl basic amino acids such as NF-lauroyl-L-lysine, Nε-palmitoylicine, Nα-paritoyl olnitine, Nα-lauroyl arginine, Nα-hydrogenated tallow fatty acid acylarginine; N-acylpolypeptides such as N-lauroyl glycylglycine; α-aminocaprylic acid, α-amino fatty acids such as α-aminolauric acid; Polyethylene, polypropylene, nylon, polymethyl methacrylate, polystyrene, divinylbenzene-styrene copolymer, ethylene tetrafluoride, and the like.

Examples of the ultraviolet absorbers may include paraaminobenzoic acid, ethyl paraaminobenzoate, amyl paraaminobenzoate, octyl paraaminobenzoate, ethylene glycol salicylate, phenyl salicylate, octyl salicynic, benzyl salicynic, butylphenyl salinic, homomentyl salicynic, benzyl cinnamon, parametoxylpic acid 2-ethoxyethyl, octyl parametoxypic acid, diparametoxylpic acid mono2-ethylhexaglyceryl, parametoxylpic acid isopropyl, diisopropyl diisopropyl cincipitic acid ester mixture, urocannic acid, ethyl urocaninate, hydroxymethoxybenzophenone, hydroxymethoxybenzophenone sulfonic acid and salts thereof, dihydroxymethoxybenzophenone, dihydroxymethoxybenzophenone sodium disulfonate, dihydroxybenzophenone, tetrahydroxybenzophenone, 4-tert-butyl-4'-methoxydibenzoylmethane, 2,4,6-Trianilino-p-(carbo-2'-ethylhexyl1'-oxy)-1,3,5-triazine, 2-(2-hydroxy-5-methylphenyl) benzotriazole and the like.

Examples of the disinfectants may include hinokithiol, triclosan, trichlorohydroxydiphenyl ether, chlorhexidine gluconate, phenoxyethanol, resorsin, isopropylmethylphenol, azulene, salicilic acid, zincphyllithione, benzalkonium chloride, photoresist No. 301, mononitroguacol sodium, undecyrenic acid, and the like.

Examples of the antioxidants may include butylhydroxyanisole, propyl gallic acid, elisorbic acid, and the like.

Examples of the pH adjusters may include citric acid, sodium citrate, malic acid, sodium malate, fumaric acid, sodium fumarate, succinic acid, sodium succinate, sodium hydroxide, sodium monohydrogen phosphate, and the like.

Examples of the alcohols may include high-grade alcohols such as cetyl alcohol.

Additional components that can be added are not limited thereto. In addition, any of the above components can be added within a range that does not impair the object and effect of the present invention, but it may be added preferably 0.01 to 5% by weight with respect to the total weight, more preferably 0.01 to 3% by weight.

The cosmetic composition of the present invention may be formed as a solution, an emulsion, a viscous mixture, or the like.

Examples of the forms of the cosmetic compositions are not particularly limited thereto. For example, they can be in the form of emulsions, creams, lotions, packs, foundations, lotions, beauty solutions, hair cosmetics, soaps, and the like.

Examples of the cosmetic compositions of the present invention may include face wash cream, face wash foam, cleansing cream, cleansing milk, cleansing lotion, massage cream, cold cream, moisture cream, latex, lotion, pack, after-sale saving cream, anti-sun-tan cream, sun-tan oil, soap, body shampoo, hair shampoo, hair rinse, hair treatment, wool, hair cream, hair liquid, set lotion, hairspray, hair bridge, color rinse, color spray, permanent wave liquid, press powder, loose powder, eye shadow, hand cream, lipstick, and the like.

The cosmetic composition of the present invention may be obtained by adding the recombinant exosome according to the present invention as an active ingredient and one or more additional components selected from the group consisting of water-soluble vitamins, soluble vitamins, polymer peptides, polymer polysaccharides, sphingolipids and seaweed extracts (such as compounding ingredients that may be added in addition to those illustrated above) by using a known method, for example, "Transdermal Application Formulation Development Manual" Matsumoto Michio Supervisory First Edition (Seishi Seowon 1985).

According to another aspect of the present invention, there is provided a method of treating wound or ulcer, which comprises administering a therapeutically effective amount of the recombinant exosome to a subject having wound or ulcer.

In the above treatment method, the ulcer may be gastric ulcer, lower limb ulcer, skin ulcer, genital ulcer, mouth ulcer, esophageal ulcer, bladder ulcer, gallbladder ulcer, foot ulcer, duodenal ulcer, gastric ulcer, or colon ulcer.

According to another aspect of the invention, there is provided a use of the recombinant exosome for the preparation of a pharmaceutical composition for treating symptoms that require epithelial cell proliferation.

In the above application, the symptoms may be selected from the group consisting of wounds, burns, scars, keloid skin, eczema, psoriasis, acne, ulcers, dermatitis, rosacea, and atopic diseases.

According to another aspect of the present invention, there is provided a use of the recombinant exosome for the preparation of a functional cosmetic for regenerating skin, relieving skin aging, or improving wrinkles.

The pharmaceutical composition may further comprise one or more pharmaceutically acceptable carriers or excipients. In addition, the pharmaceutical composition may have various formulations (e.g., oral or parenteral formulations), but preferably a parenteral formulation. In addition, when applied to skin wounds, it may be preferable to be a topical application-type agent. When formulating a pharmaceutical composition according to an embodiment of the present invention, it is prepared using a diluent or excipient such as a filler, extender, binder, wetting agent, disintegrant, surfactant, or the like. Solid preparations for oral administration may include tablets, pills, acids, granules, capsules, and the like, which solids are prepared by mixing at least one or more excipients such as starch, calcium carbonate, sucrose or lactose, gelatin, and the like. In addition to simple excipients, lubricants such as magnesium stearate, talc, and the like may also be used. Liquid preparations for oral administration may include suspension agents, anti-solution agents, emulsions, syrups, and the like, and in addition to water and liquid paraffin, which are commonly used simple diluents, various excipients, such as wetting agents, sweeteners, fragrances, preservatives, and the like. Preparations for parenteral administration may include sterile aqueous solutions, non-aqueous solvents, suspensions, emulsions, lyophilized agents, and suppositories. Non-aqueous solvents or suspension solvents may include propylene glycol, polyethylene glycol, vegetable oils such as olive oil, injectable esteros such as ethyl oleate, and the like. As a substrate for suppositories, witepsol, macrogol, tween 61, cacaoji, laurinji, glycerogelatin, and the like may be used.

The pharmaceutical composition may be in a formulation selected from the group consisting of tablets, pills, acids, granules, capsules, suspensions, solutions, emulsions, syrups, sterilized aqueous solutions, non-aqueous solvents, suspensions, emulsions, lyophilized agents, and suppositories.

The pharmaceutical compositions of the present invention may be administered orally or parenterally, and when administered parenterally, it is possible to administer through various routes such as intravenous injection, intranasal inhalation, intramuscular administration, intraperitoneal administration, transdermal absorption, and the like.

The compositions of the present invention are administered in a therapeutically effective amount.

As used herein, the term "therapeutically effective amount" means an amount sufficient to treat a disease at a reasonable benefit/risk ratio applicable to medical treatment, and the effective dose level is determined by considering many factors including type of a subject, severity, age, sex, activity of the drug, sensitivity to the drug, time of administration, route of administration and rate of excretion, duration of treatment, concomitant drugs, and other well-known factors in the medical field. The pharmaceutical compositions of the present invention may be administered at a dose of 0.1 mg/kg to 1 g/kg, more preferably at a dosage of 1 mg/kg to 500 mg/kg. On the other hand, the dose can be appropriately adjusted according to the age, gender, and condition of the subject.

EXAMPLES

Hereinafter, the present invention will be described in more detail through examples and experimental examples. However, the present invention is not limited to the embodiments and experimental examples disclosed below, but may be implemented in various different forms, and the following embodiments and experimental examples are provided to ensure that the disclosure of the present invention is complete, and to fully inform those skilled in the art of the scope of the invention.

Figure 2A:
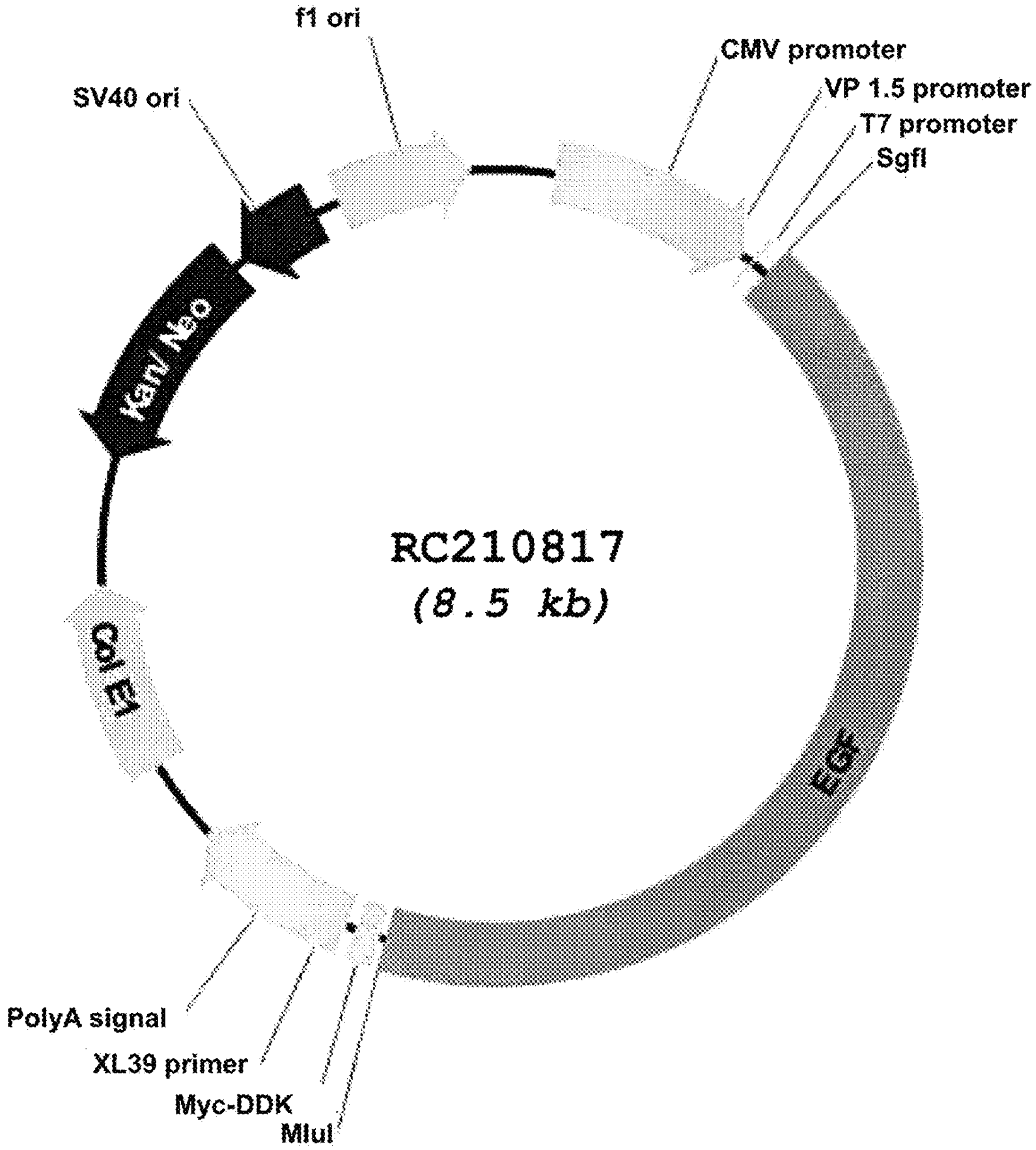
FIG. 2A shows the map of an RC210817 plasmid (top) that is used to clone a genetic construct comprising a full-length EGF (preEGF) prepared according to an embodiment of the present invention and a gene map (bottom) that includes cloning sites.

Example 1: Preparation of Recombinant Exosomes Comprising Membrane-Bound EGFs A DNA construct (RC210817, Origene, FIG. 2*a*) including a polynucleotide sequence (SEQ ID NO: 2) encoding a full-length EGF protein (preEGF) (SEQ ID NO: la) was introduced into a pCMV6-Entry vector, and HEK293T cells were transfected with the vector. Specifically, HEK293T/17 cells ($6\times10^6$) were cultured in the condition of 37° C. and 5% $CO_2$ on a high glucose medium (Dulbecco's modified Eagle's medium, DMEM, and 4,500 mg/L glucose) with 10% FBS and 1% antibacterial agent added. When the confluency reached 80-90% in a 15 cm petri dish, the medium was replaced with a serum-free DMEM medium with glutamax (Gibco) added. After 2 hours, the cells were transfected with a plasmid DNA (20 μg) comprising a polynucleotide sequence encoding the full-length EGF (preEGF) by using a transfection reagent (PEI) according to the manufacturer's instructions. 48 hours after the transfection, in order to isolate exosomes, the supernatant of the cell culture was obtained by differential centrifugation, as described below in detail.

First, in order to remove cell debris and other cell components from the culture medium containing exosomes, the culture medium was sequentially centrifuged at 300×g for 10 minutes, 2000×g for 10 minutes, and 10000×g for 30 minutes. The culture medium was filtered with a 0.22 m filter and then ultra-centrifugated at 150,000×g for 2 hours by using 70 Ti rotor (Beckman Instruments). The thus obtained recombinant exosomes (hereinafter abbreviated as 'preEGF-Exo') containing the full-length EGF were resuspended in PBS containing a protease inhibitor (Roche), and the protein concentration of the isolated exosome was measured by using a BCA protein analysis kit (Bio-Rad).

Example 2: Preparation of Recombinant Exosomes Comprising EGF Variants Displayed on the Surface of the Exosomes, Wherein the EGF Variants Contain PDGFR Transmembrane Domains Whether the recombinant EGF membrane protein in which a mature EGF was linked to the transmembrane domain of EGF or to a transmembrane domain derived from another transmembrane protein exhibits a cell proliferation effect as much as the full-length EGF does was determined.

Figure 1B:
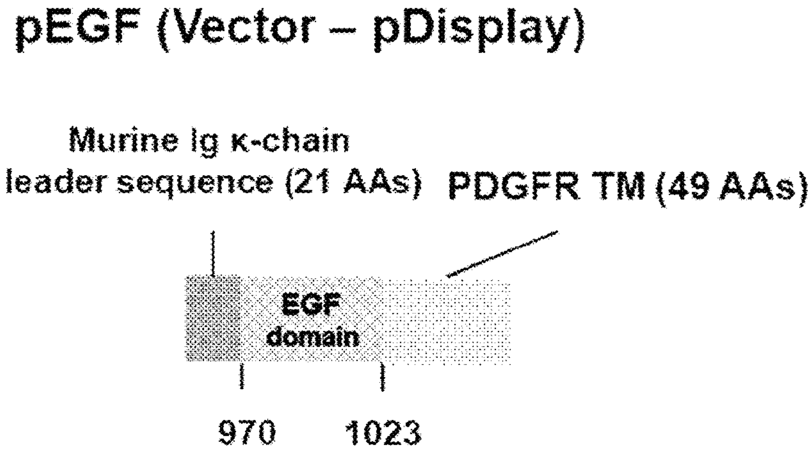
FIG. 1B shows the structure of an EGF variant (pEGF) according to an embodiment of the present invention, in which the mature form (EGF domain) of EGF linked to the signal sequence of the Ig κ-chain of a rat is fused with the transmembrane domain of PDGFR.
Figure 1C:
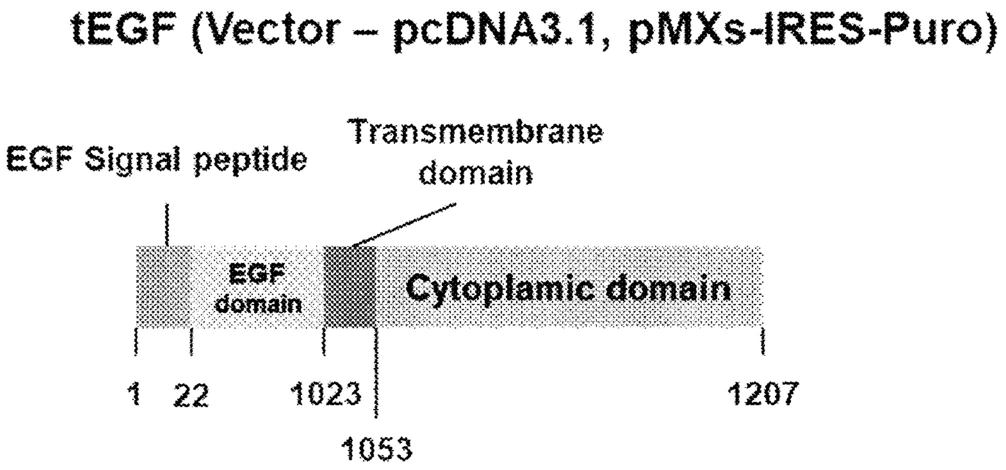
FIG. 1C schematically shows the structure of an EGF variant (tEGF) according to an embodiment of the present invention, in which the mature form (EGF domain) of EGF linked to the signal sequence of EGF is linked to the transmembrane domain and the cytoplasmic domain of EGF.

To this end, a gene construct (SEQ ID NO: 4) encoding a recombinant mature EGF (SEQ ID NO: 3, FIG. 1B) in which the mature EGF was linked to IgK peptide (i.e., the signal peptide of a pDisplay vector (Thermofisher Scientific, Inc., USA)) and to the PDGFR transmembrane domain was introduced into the pDisply vector. By using the method described in Example 1, HEK293T/17 cells were transfected with the vector, and the recombinant exosomes were isolated and named 'pEGF-Exo.'

Example 3: Preparation of Recombinant Exosomes Comprising EGF Variants Displayed on the Surface of the Exosomes, Wherein the EGF Variants Contain PDGFR Transmembrane Domains and the Cytoplasmic Domains of EGF A gene construct (SEQ ID NO: 6) encoding a cleaved type EGF (SEQ ID NO: 5, 1C) was prepared. The cleaved type EGF was prepared by removing (truncating) a cleavage site from the full-length EGF. The cleavage site was responsible for cleaving the full-length EGF at the position between the Prepro peptide portion and the transmembrane domain of the mature EGF. The gene construct was inserted into a pcDNA3.1 vector (Thermofisher Scientific Inc., USA). By using the method described in Example 1, HEK293T/17 cells were transfected with the vector, and the recombinant exosomes were isolated and named 'tEGF-Exo.'

Example 4: Preparation of Stable Cell Lines Expressing EGF Variants

Figure 2B:
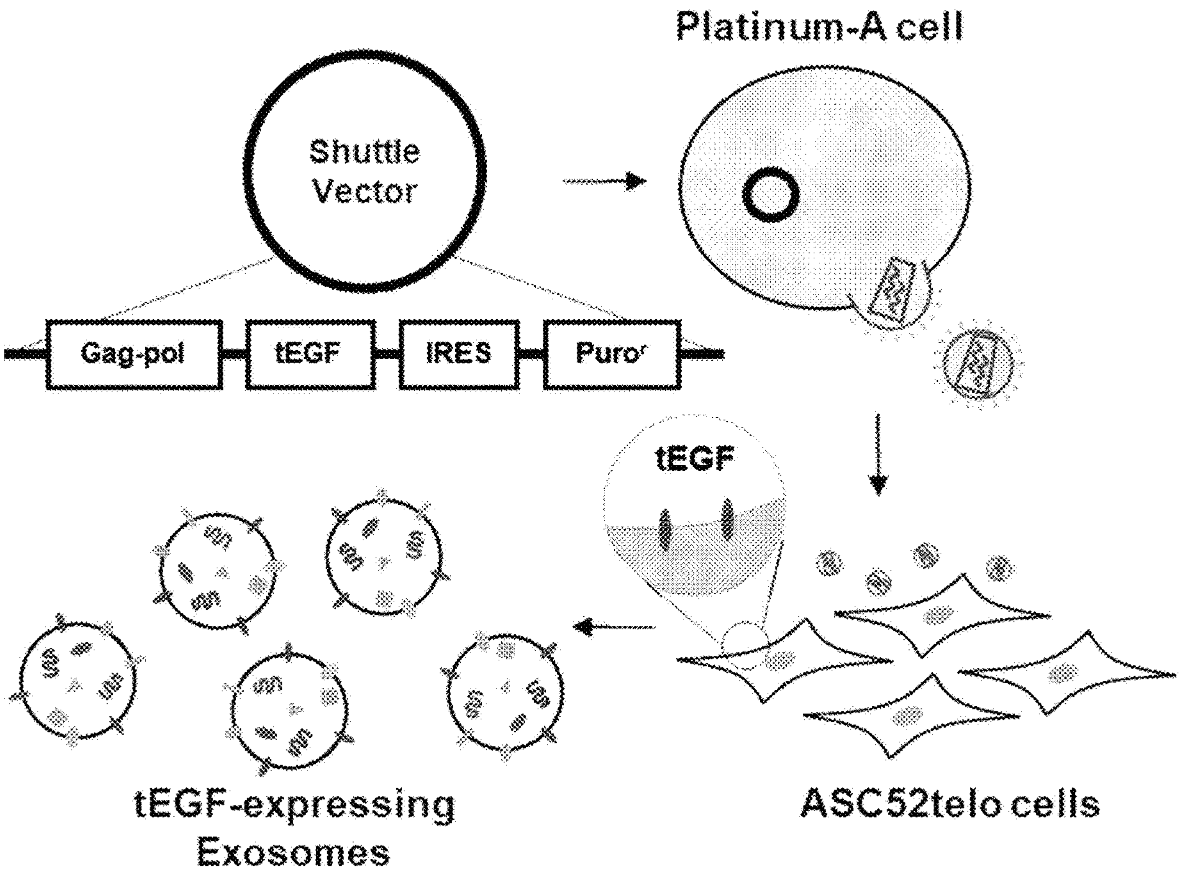
FIG. 2B shows a retroviral vector used for the preparation of recombinant exosomes of Example 4, which are isolated from mesenchymal stem cells and comprise EGF on the membrane surface thereof and schematically shows a process of preparing a stable cell line that is used to prepare the recombinant exosomes using the vector.

The gene construct prepared in Example 3 was inserted into a pMXs-IRES-Puro retroviral vector (Cell Biolabs, USA) to prepare a plasmid DNA (FIG. 2B) for expressing EGF variants.

Plat-A cells were cultured with $6\times10^6$ cells per 150 mm petri dish. The culture medium was replaced with serum-free DMEM. The cells were transfected with 20 μg of the thus prepared plasmid DNA for expressing EGF variants in combination with 80 μg of PEI, and the cells were cultured for 24 hours. The culture medium was replaced with antibiotic-free DMEM containing 10% bovine fetal serum, and the cells were incubated for 48 hours. Viral particles comprising the gene construct were obtained by centrifuging the cell culture supernatant at 3000 rpm and filtering with a 45 m filter. Then, mesenchymal stem cells (ASC52telo cells, ATCC) were incubated with 4 μg/ml of polybrene (Sigma-Aldrich) with the medium containing the viral particles for 48 hours, and then they were cultured with medium containing 5 μg/ml of puromycin for selecting the transformed cells.

The separation of the exosome was performed in the same method as in Example 1, and the isolated exosome was named 'stEGF-Exo'.

Experimental Example 1: Characterization of Recombinant Exosomes

The quality and characteristics of the recombinant exosomes (preEGF-Exo, pEGF-Exo, and tEGF-Exo) prepared according to Examples 1 to 3 were confirmed using Western blat (WB), flow cytometry, dynamic light scattering (DLS) analysis, and cryogenic transmission electron microscopy as described below.

1-1: Exosome Marker Expression Analysis

First, for Western Blot analysis, the super-centrifuged recombinant exosome pellets were dissolved using RIPA buffer (Cell Signaling Technology) comprising a Protease Inhibitor Cocktail (Calbiochem), and the same amount of exosome protein (10 μg) was analyzed with SDS-PAGE and transferred to nitrocellulose membranes. Thereafter, an anti-EGF antibody (1:1000, Abcam, ab9695) was added to detect the expression of EGF and left overnight at 4° C., and anti-Alix antibodies (1:500, Santa Crus, sc-99010) and anti-Tsg 101 antibodies (1:500, Santa Crus, sc-22774) were used as exosome markers. An HRP-bound secondary antibody (1:4000, Sigma-Aldrich) was then added and visualized by chemiluminescence.

Figure 3A:
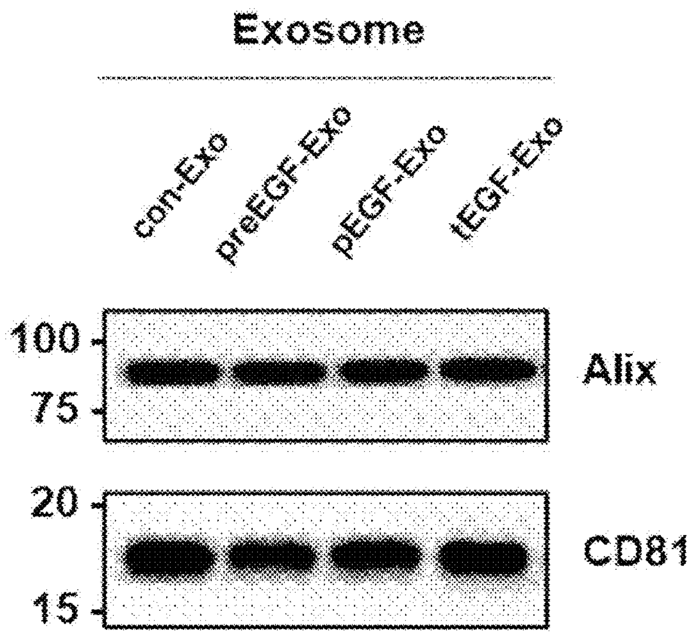
FIG. 3A is a photograph showing the results of Western Blot analysis of various recombinant exosomes (con-Exo, preGEG-Exo, pEGF-Exo, and tEGF-Exo) of embodiments of the present invention.

As shown in FIG. 3A, it was confirmed that all of the recombinant exosomes of the present invention normally expressed exosome markers (Alix and CD81).

1-2: Investigation of Whether EGF was Expressed on Membrane Surface

Whether the various recombinant exosomes comprising the various forms of membrane-bound EGF proteins prepared in Examples 1 to 3 actually contain EGFs on the membrane of the exosomes was investigated.

A flow cytometer is commonly used to identify whether a specific protein is expressed on the membrane of a cell. However, because exosomes are very small, they cannot be analyzed directly with a flow cytometer. Latex beads have been known to be used to overcome the problem.

Accordingly, the recombinant exosomes (preEGF-Exo, pEGF-Exo, and tEGF-Exo) prepared in Examples 1 to 3 were reacted with latex beads (Invitrogen, USA) according to the manufacturer's protocol, and thereafter anti-EGF antibodies (1:200, Abcam, ab9695) were added to detect exosome membrane expression of EGF and left for 1 hour at a condition of 4° C. The resultant was washed with PBS, and Alexa 647-bound secondary antibody (1:200, Jackson ImmunoResearch) was added. After 1 hour at room temperature, the degree of EGF expressed on exosome surface was analyzed by using a flow cytometer.

Figure 3B:
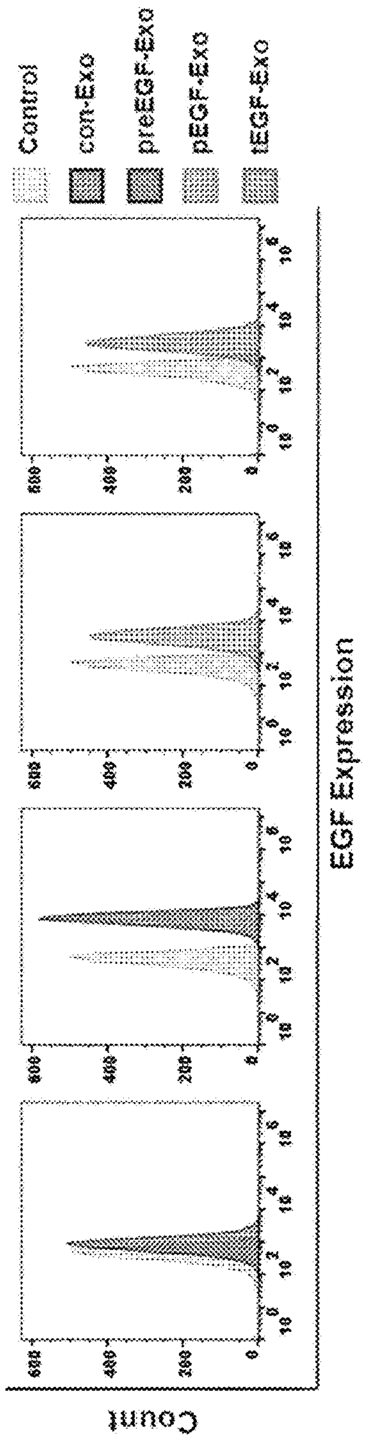
FIG. 3B is a histogram representing the results of flow cytometry analysis that is performed by using latex beads to show whether EGF is expressed in the exosomes.

It was confirmed that all of the recombinant exosomes (preEGF-Exo, pEGF-Exo, and tEGF-Exo) according to various embodiments of the present invention had EGFs expressed on the membrane surface (FIG. 3B).

1-3: Dynamic Light Scattering Analysis

The size distribution of the recombinant exosomes was analyzed by dynamic light scattering (DLS) using Zetasizer Nano ZS (Malvern Instruments, Ltd., UK), and the exosome sizes were analyzed through a number ratio (z-average) at a fixed angle of 173 under 25° C. using a software provided with the instrument.

Figure 3C:
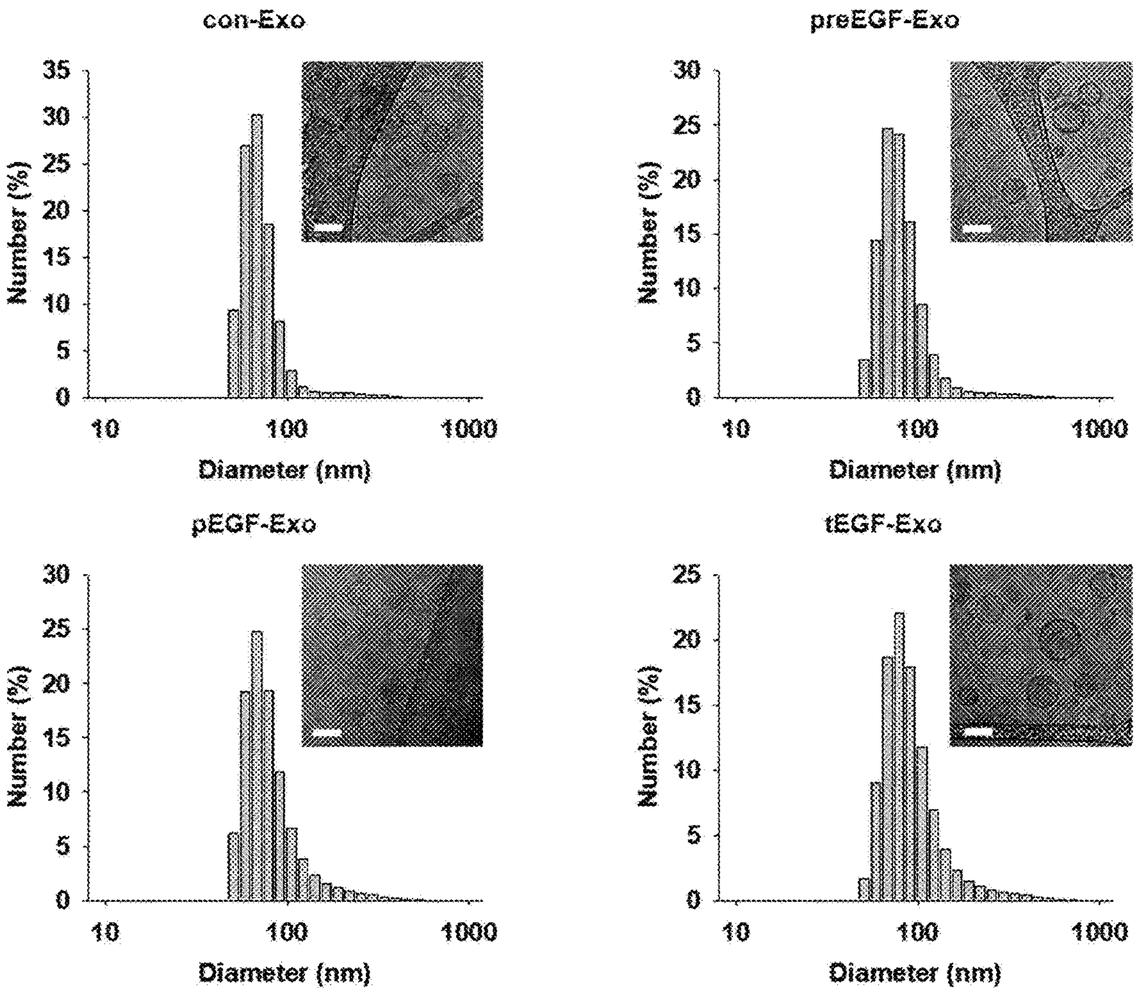
FIG. 3C shows the results of dynamic light scattering analysis and cryogenic transmission electron microscopy of the exosomes.

As shown in FIG. 3C, it was confirmed that all of the recombinant exosomes prepared in Examples 1 to 3 had a normal exosome size distribution of about 100 nm in average size.

1-4: Cryogenic Transmission Electron Microscopy

Cryogenic transmission electron microscopy was used to confirm the morphology of the recombinant exosomes. To this end, the sample was placed on copper grids equipped with carbon film (Electron microscopy science), stained negatively using uranyl acetate solution, and then photographed using transmission electron microscopy (Tecnai, USA).

It was confirmed that the morphology of the recombinant exosomes was normal as shown at the top right of the graph of the dynamic light scattering analysis (FIG. 3C).

Experimental Example 2: Evaluation of Cell Proliferation Effect of Recombinant Exosomes Containing EGFs Displayed on Membrane Surface It is known that EGF shows its activity only when it is formed as a mature form by truncation. Whether the full-length EGF bound to the exosome membrane has cell proliferation ability was investigated.

Figure 4A:
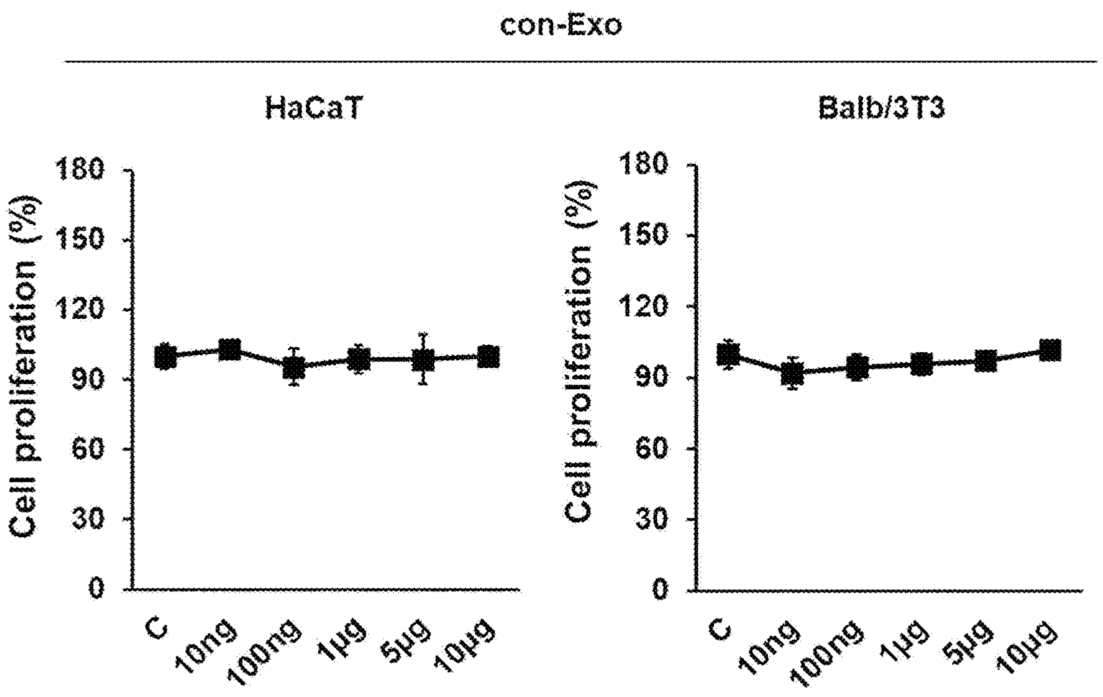
FIG. 4A graphically shows the degree of the cell proliferation that occurs in HaCaT human keratinocytes (left) and Balb/3T3 mouse fibroblasts (right) when various concentrations of control exosomes (con-Exo) obtained from untransfected cells are treated to HaCaT human keratinocytes and Balb/3T3 mouse fibroblasts.

First, exosomes extracted from HEK293T/17 cells (control exosomes; 'con-Exo') at various concentrations (10 ng/ml, 100 ng/ml, 1 μg/ml, 5 μg/ml, and 10 μg/ml) were treated to HaCaT human keratinocytes and Balb/3T 3 mouse fibroblasts. After 24 hours later, the degree of cell proliferation was analyzed using a cell counting kit (Donjindo Molecular Technolgodies, Inc., USA). As shown in FIG. 4A, it was determined that control exosomes (con-Exo) extracted from the non-transfected cells had no effect on cell proliferation.

Next, the recombinant exosomes (wtEGF-Exo) obtained in Example 1 at various concentrations (10 ng/ml, 100 ng/ml, 1 μg/ml, 5 μg/ml, and 10 μg/ml) were treated to Balb/3T 3 mouse fibroblasts and HaCaT human keratinocytes. After 24 hours later, the degree of cell proliferation was analyzed using the cell counting kit (Donjindo Molecular Technolgodies, Inc., USA).

Figure 4B:
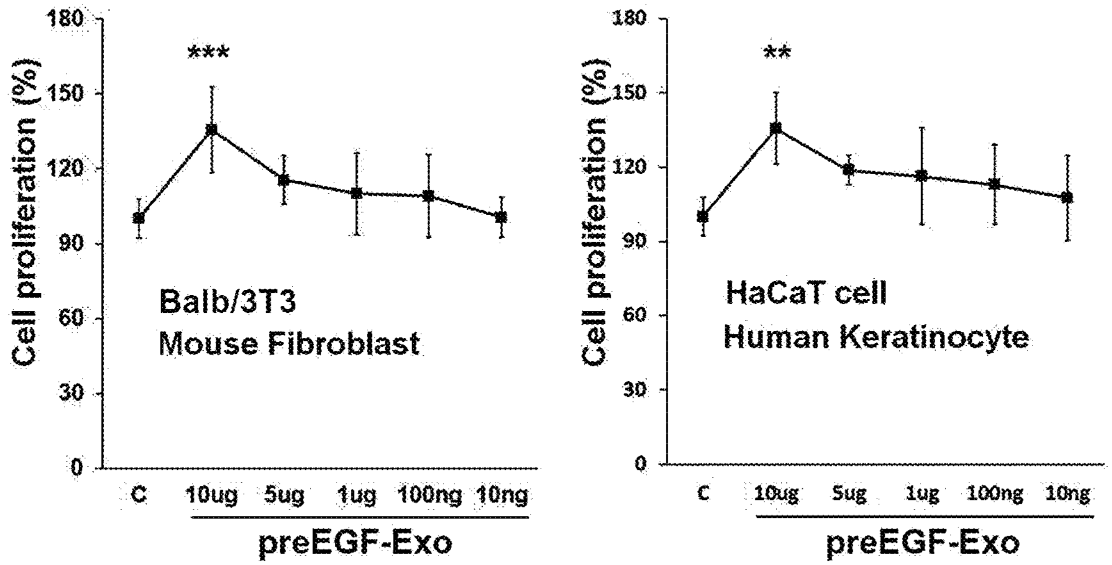
FIG. 4B graphically shows the degree of the cell proliferation that occurs in HaCaT human keratinocytes (right) and Balb/3T3 mouse fibroblasts (left) when various concentrations of recombinant exosomes (preEGF-Exo) according to embodiments of the present invention are treated to HaCaT human keratinocytes and Balb/3T3 mouse fibroblasts.

As shown in FIG. 4B, the recombinant exosomes exhibited concentration-dependent cell proliferation ability in both mouse fibroblasts and human keratinocytes. In particular, at the concentration of 10 μg/ml, the cell proliferation effect of the recombinant exosomes was significantly higher than that of the control group. These results are surprisingly contrary to the conventional knowledge that a precursor EGF does not exhibit the function of EGF.

Subsequently, whether the recombinant exosomes prepared in Examples 2 and 3 also exhibit cell proliferation effects was investigated. The recombinant exosomes at various concentrations (1 μg/ml and 10 μg/ml) were treated to HaCaT human keratinocytes. The degree of cell proliferation was analyzed in the method as described above.

Figure 4C:
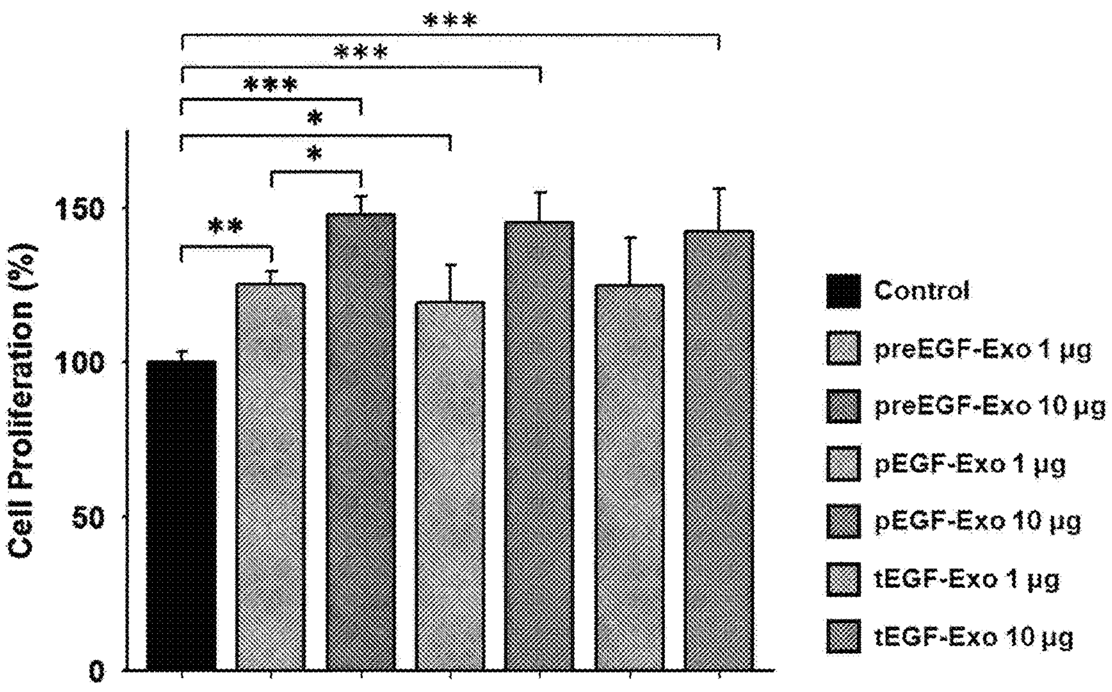
FIG. 4C graphically shows the degree of cell proliferation that occurs after 1 g/ml and 10 μg/ml of various recombinant exosomes (preEGF-Exo, pEGF-Exo, and tEGF-Exo) according to embodiments of the present invention are treated.

As shown in FIG. 4C, all of the recombinant exosomes according to various embodiments of the present invention exhibited concentration-dependent cell proliferation ability.

It is thus suggested that EGFs displayed on the surface of exosome membranes can have superior effects in areas requiring EGF activity (e.g., wound treatment effect) compared to free form EGFs.

Experimental Example 3: Cell Mobility Evaluation

It is known that the migration of skin cells plays the most important role in the skin regeneration process. Scratch wound healing assay was performed to confirm the effect on cell migration of the recombinant exosomes comprising EGFs displayed on exosome membrane surface according to embodiments of the present invention.

Specifically, HaCaT human keratinocytes were cultured until 80% confluency was reached in a 100 mm dish at the time of 7-th generation cultivation. HaCaT human keratinocytes isolated using 0.25% trypsin-EDTA in 6-well plates were spread as many as 3×10 5 cells per well. After the cells were incubated at 37° C. overnight, the wells were washed twice with DPBS to scratch cells and remove debris using a 200 μL pipette tip. Then, 0.5 mL medium containing 10% FBS and containing no exosomes and 10 μg/ml of the recombinant exosomes prepared in Examples 1 and 2 were added to each well. After the cells were incubated at 37° C. for 24 hours, the scratched part was placed under a microscope (Leica, Wetzlar, Germany). Scratch width was measured using an Image-Pro Plus software, Media Cybernetics, USA.

Figure 5A:
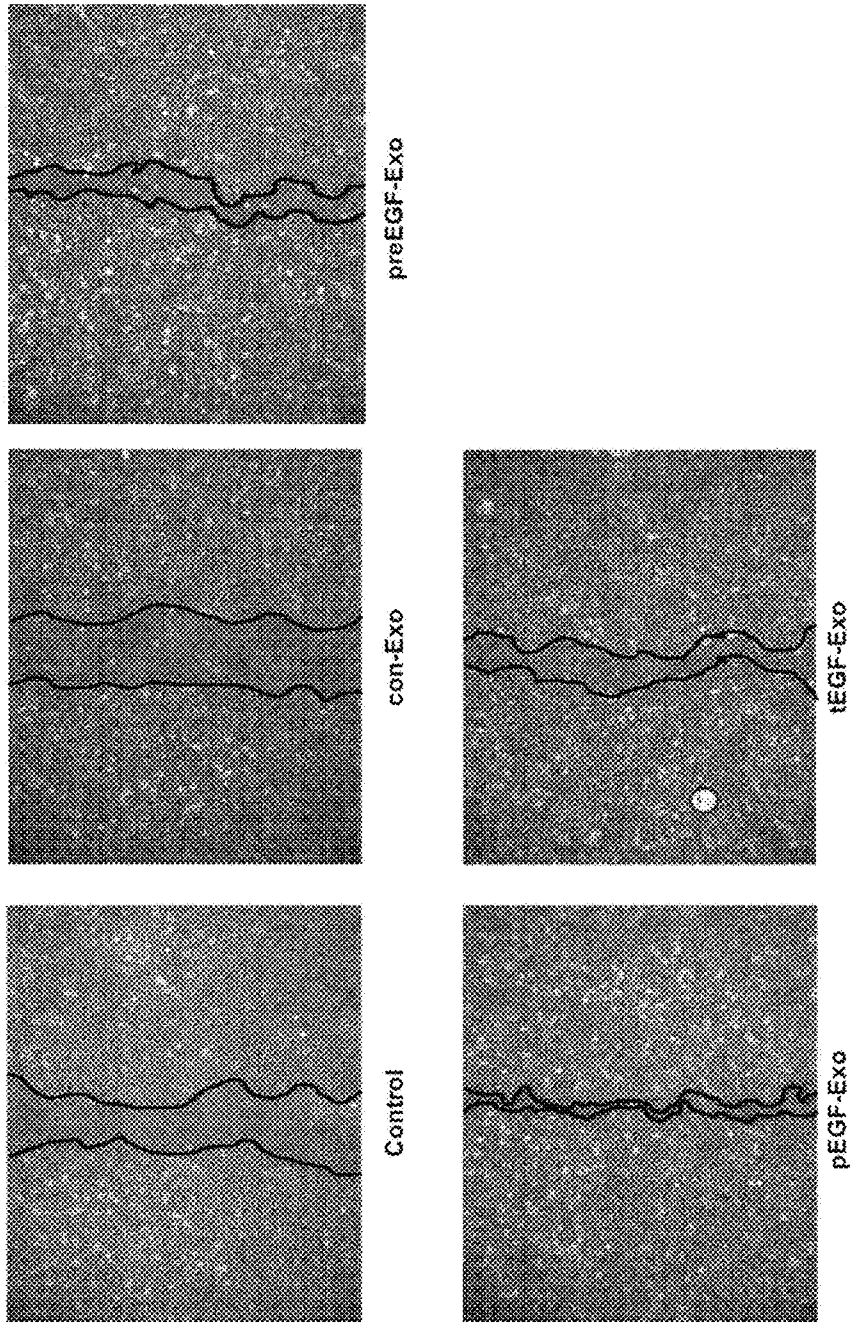
FIG. 5A represents microscopic photographs showing the degree of wound recovery that occurs 24 hours after control PBS, various recombinant exosomes (preEGF-Exo, pEGF-Exo, and tEGF-Exo) according to embodiments of the present invention, and control exosomes (con-Exo) are treated to HaCaT human keratinocytes with scratches induced.
Figure 5B:
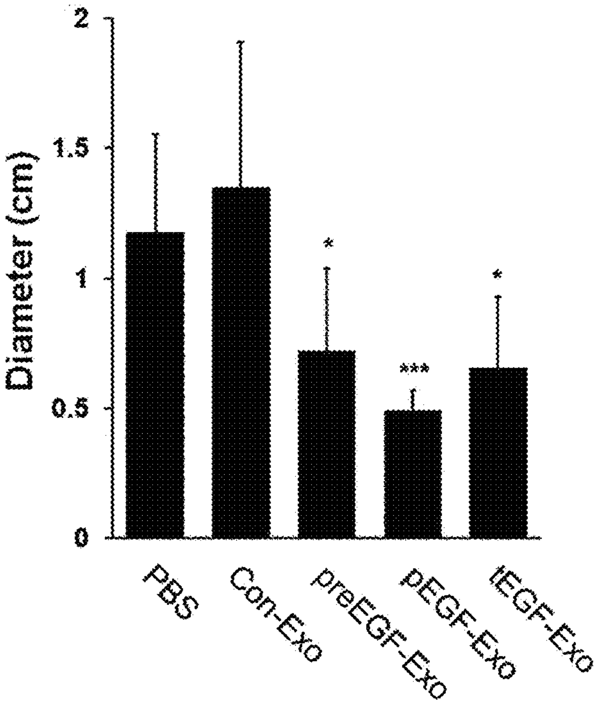
FIG. 5B represents a graph quantifying the results shown in FIG. 5A.

As shown in FIGS. 5A and 5B, the recombinant exosomes comprising membrane-bound EGFs according to embodiments of the present invention significantly promoted cell mobility toward scratched would sites compared to the control groups.

In addition, scratch wound healing assay was also performed on Balb/3T3 cells in the method as described above.

Figure 5C:
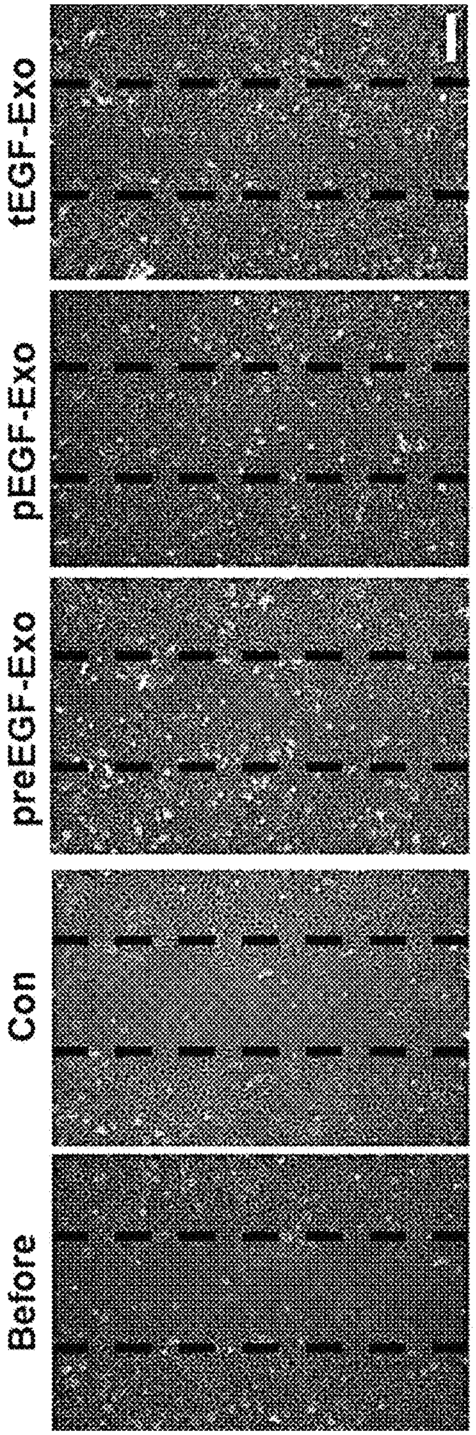
FIG. 5C represents microscopic photographs showing the degree of wound recovery that occurs 24 hours after various recombinant exosomes (preEGF-Exo, pEGF-Exo, and tEGF-Exo) according to embodiments of the present invention and control exosomes (con-Exo) are treated to Balb/3T3 mouse fibroblasts with scratches induced.
Figure 5D:
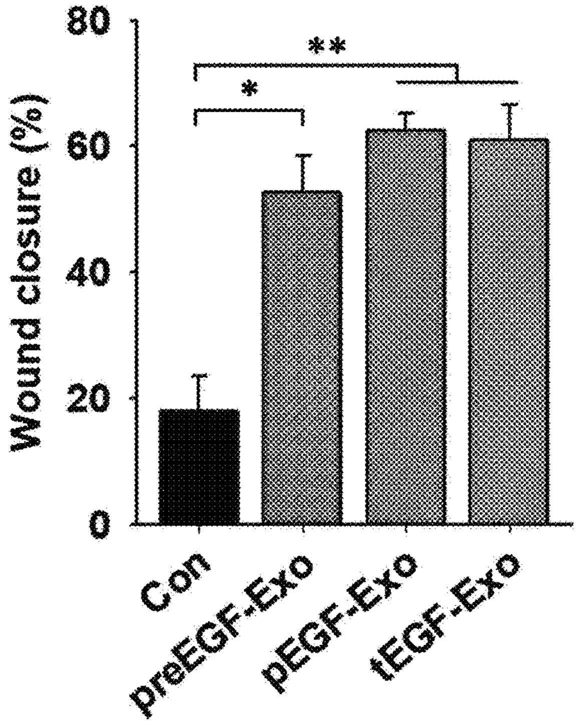
FIG. 5D represents a graph quantifying the results shown in FIG. 5C.

As shown in FIGS. 5C and 5D, the recombinant exosomes according to embodiments of the present invention showed significantly better wound healing ability than the control groups. In particular, the wound healing effect of the recombinant exosomes of Examples 2 and 3, in which the activated form of the EGF protein is linked to the transmembrane domain of PGDFR was higher than that of the recombinant exosome of Example 1.

Figure 6A:
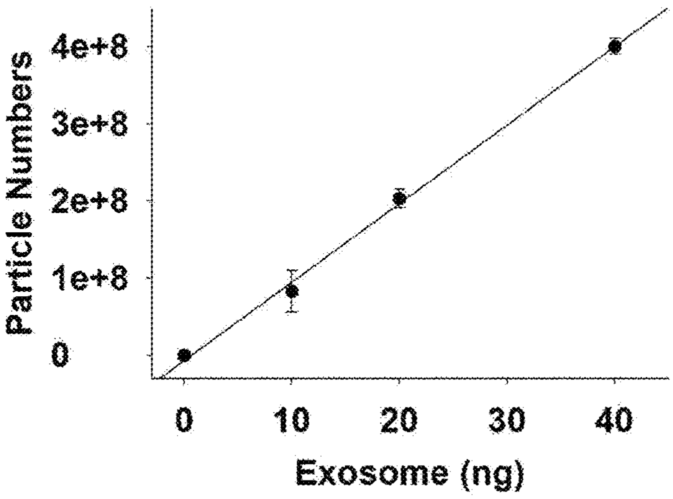
FIG. 6A is a graph showing the results of nanoparticle tracking analysis (NTA) performed to confirm how many particles per a reference weight the recombinant exosomes have.
Figure 6B:
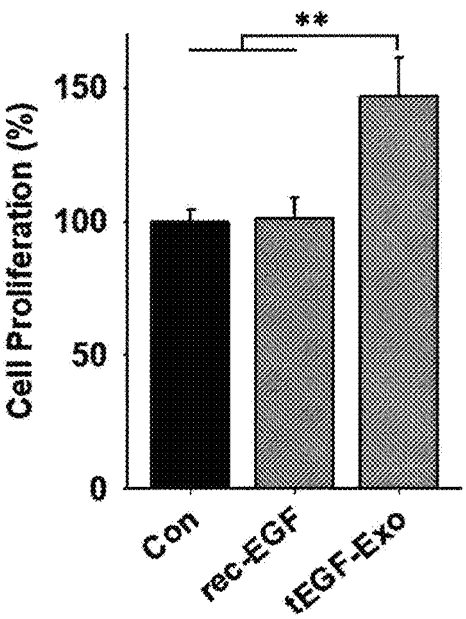
FIG. 6B is a graph showing the effect of cell proliferation that occurs 24 hours after the recombinant exosomes (tEGF-Exo) according to embodiments of the present invention and the recombinant EGF having the same molar concentration as the recombinant exosomes (tEGF-Exo) are treated to HaCaT cells.

Experimental Example 4: Particle Count Analysis of Recombinant Exosome Having EGFs Displayed on Membrane Surface Nanoparticle Tracking Analysis (NTA) was performed according to the manufacturer's instructions using the NanoSight NS300 device of Marvel Analytic Corporation (USA) in order to determine how many exosomes exist in 1 μg of recombinant exosomes. As shown in FIG. 6A, it was determined that $10^{10}$ exosomes existed in 1 μg of EGF-Exosome. Thereafter, the cell proliferation efficacy of the recombinant EGF protein of the same molar concentration as the EGF present in the 10 μg of EGF-Exosome was assayed using the method of Experimental Example 2 on HaCaT human keratinocytes and compared with the cell proliferation efficacy of the EGF-Exosome. As shown in FIG. 6B, while the recombinant EGF had no effect on cell proliferation capacity, tEGF-Exo according to Example 3 showed excellent cell proliferation efficacy. This suggests that EGFs showed higher efficacy when they are displayed on exosomal membrane surface compared to when they are in a free form.

Experimental Example 5: Evaluation of Effect of Recombinant Exosomes Prepared Using Mesenchymal Stem Cells 5-1: Characterization of Recombinant Exosomes Next, the recombinant exosomes prepared using mesenchymal stem cells (MSCs, ASC52telo cells, ATCC) prepared in Example 4 were characterized. The methods described in Experimental Example 1 and Experimental Example 5 were used.

Figure 7A:
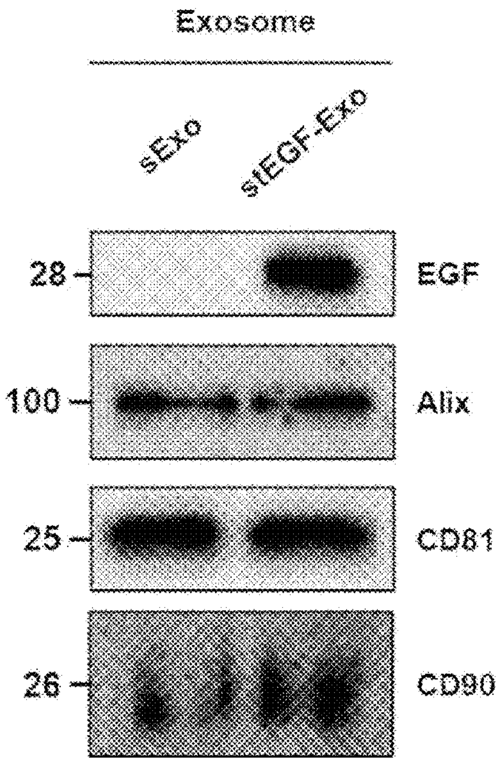
FIG. 7A represents Western Blot analysis results performed on EGF and exosome makers to compare the recombinant exosomes (stEGF-Exo) isolated from stably transfected mesenchymal stem cells according to embodiments of the present invention with control exosomes (sExo) isolated from non-transfected mesenchymal stem cells.
Figure 7B:
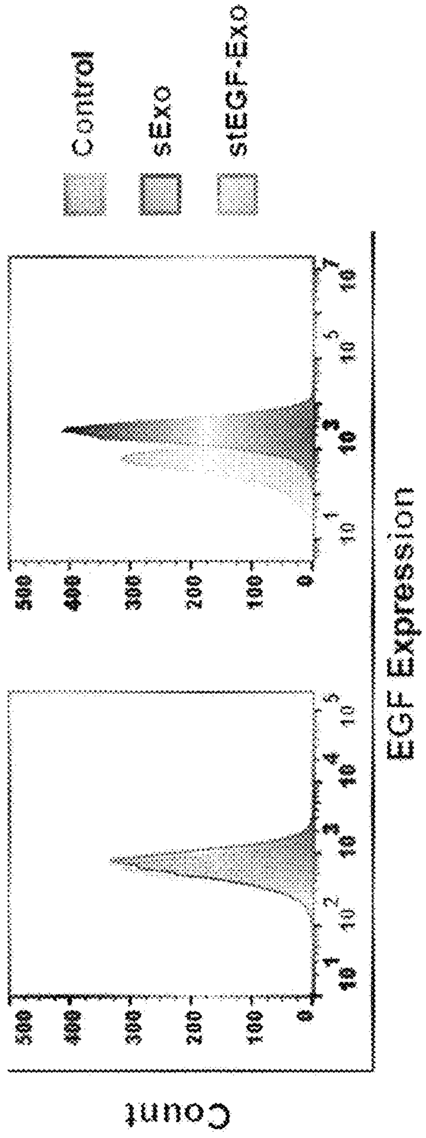
FIG. 7B is a histogram showing the results of flow cytometry performed to confirm whether the recombinant exosomes (stEGF-Exo; right) according to embodiments of the present invention and the control exosomes (sExo, left) express EGF.
Figure 7C:
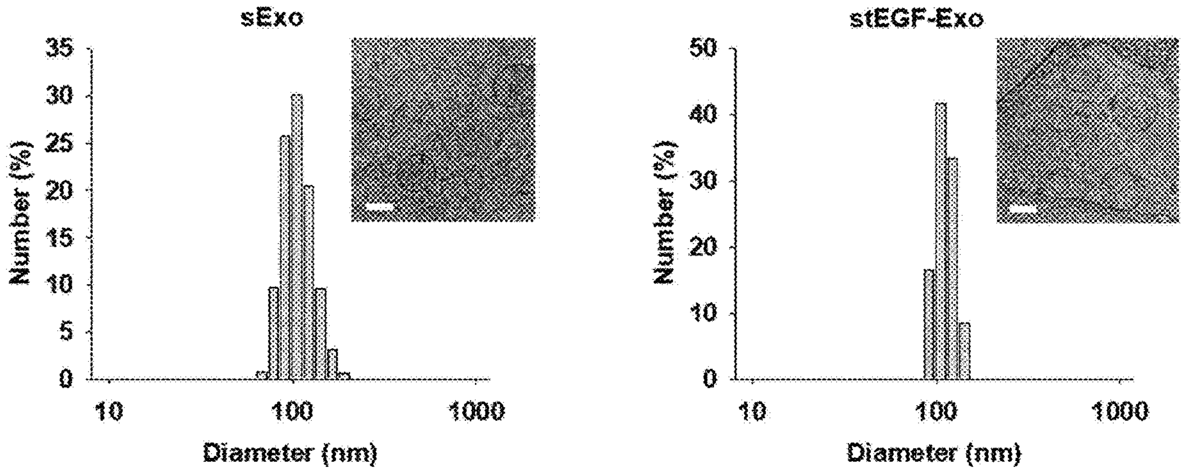
FIG. 7C represents graphs showing the results of dynamic scattering analysis performed to analyze the size distribution of the recombinant exosomes (stEGF-Exo, right) according to embodiments of the present invention and the control exosomes (sExo, left) isolated from non-transfected mesenchymal stem cells and represents cryogenic transmission electron microscopy of the respective exosomes.
Figure 7D:
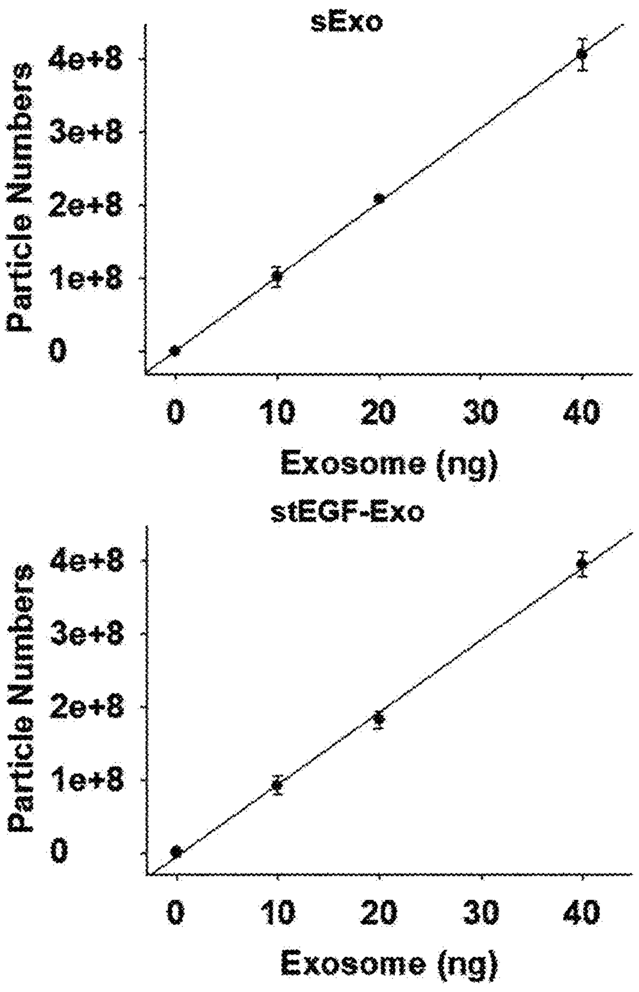
FIG. 7D represents graphs showing nanoparticle tracking analysis results performed to measure how many exosome particles per a reference weight the recombinant exosomes (stEGF-Exo, bottom) and the control exosomes (sExo, top) have, respectively.

First, Western Blot analysis was performed to analyze the exosome markers. As shown in FIG. 7A, the exosome markers Alix and CD81 and the stem cell marker CD90 were expressed both in the control exosomes (sExo) isolated from untransfected MSCs and in the recombinant exosomes (stEGF-Exo) isolated from the transfected MSCs of Example 4. In addition, it was confirmed by Western Blot analysis (FIG. 7A) and flow cytometry (FIG. 7B) that EGF was well expressed in the stEGF-Exo prepared in Example 4. In addition, as shown in FIG. 7C, it was confirmed by dynamic light scattering analysis and cryogenic transmission electron microscopy analysis that all exosomes were spherical and had a size of 30 nM to 150 nM. Also, as shown in FIG. 7D, it was confirmed by NTA analysis that $10^{10}$ exosomes existed in 1 μg of both sExo and stEGF-Exo.

5-2: Analysis of Cell Proliferation Effect

Figure 7E:
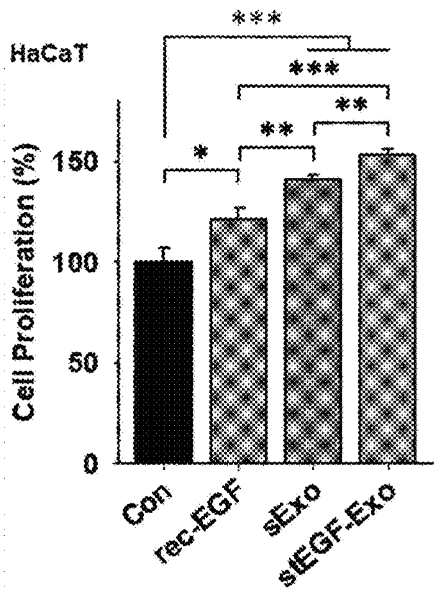
FIG. 7E represents graphs comparing the cell proliferation effect that the recombinant exosomes (stEGF-Exo) exhibit when they are treated to HaCaT human keratinocytes with the cell proliferation effect that the free form EGF (rec-Exo) exhibit when they are treated to HaCaT human keranitocytes and with the cell proliferation effect that the control exosomes (sExo) exhibit when they are treated to HaCaT human keranitocytes.
Figure 7F:
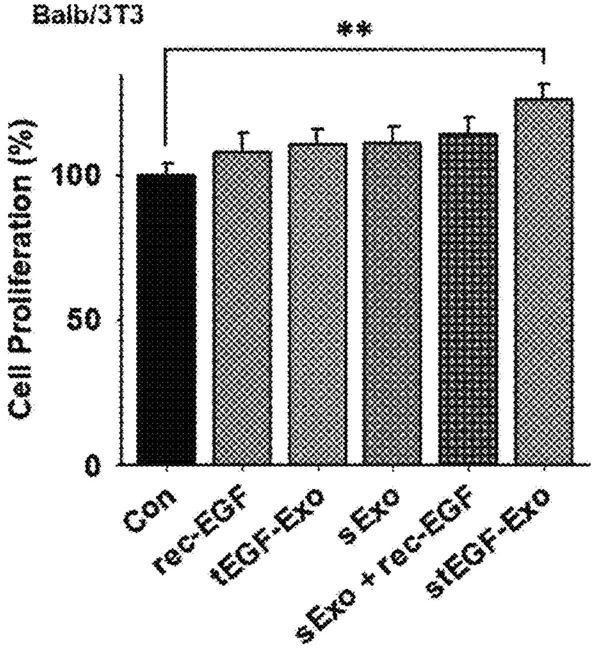
FIG. 7F represents graphs comparing the cell proliferation effect that the recombinant exosomes (stEGF-Exo) exhibit when they are treated to HaCaT human keratinocytes with the cell proliferation effects that the free form EGF (rec-Exo), the recombinant exosomes (tEGF-Exo), the control exosomes (sExo), and a combination of the free form EGF and the control exosomes (sExo+rec-EGF), respectively, exhibit when they are treated to HaCaT human keranitocytes, respectively.

Subsequently, the cell proliferation effect of the recombinant exosomes (stEGF-Exo) isolated from MSCs according to Example 4 was analyzed in the same method as used in Experimental Example 2. The cell proliferation effect of 10 μg/ml of stEGF-Exo in HaCaT cells (FIG. 7E) and Balb/3T 3 cells (FIG. 7F) was higher than 10 μg/ml of sExo and also higher than recombinant EGFs having the same molar concentration as EGFs existing in 10 μg/ml of stEGF-Exo. In addition, the cell proliferation effect of the recombinant exosomes (stEGF-Exo) prepared in Example 4 was higher than the combined effect of sExo and recombinant EGF (rhEGF), which suggests that the cell proliferation effect of EGFs is maximized when EGFs exist on exosomal surfaces.

5-3: Analysis of Wound Healing Effect

The wound healing effect of the recombinant exosomes (stEGF-Exo) prepared in Example 4 was analyzed in the same method as used in Experimental Example 3.

Figure 7G:
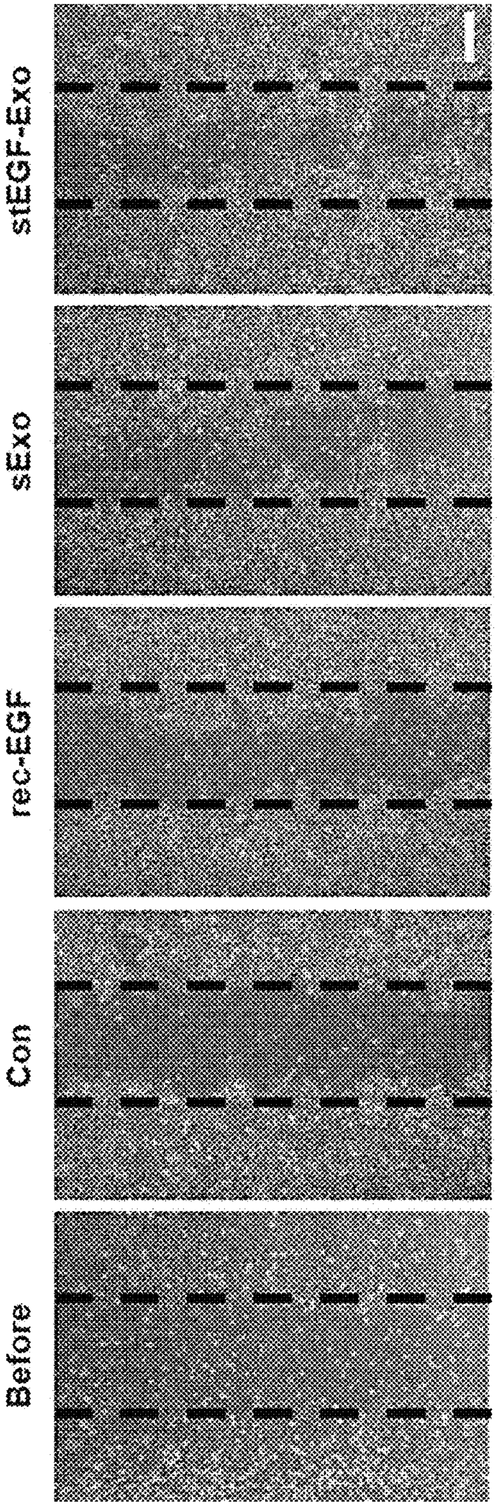
FIG. 7G represents microscopic photographs showing the degree of wound recovery that occurs 24 hours after the control PBS, the free recombinant EGF (rec-EGF), the control exosomes (sExo), and the recombinant exosomes (stEGF-Exo), respectively, are treated to HaCaT human keranitocytes with scratches induced.
Figure 7H:
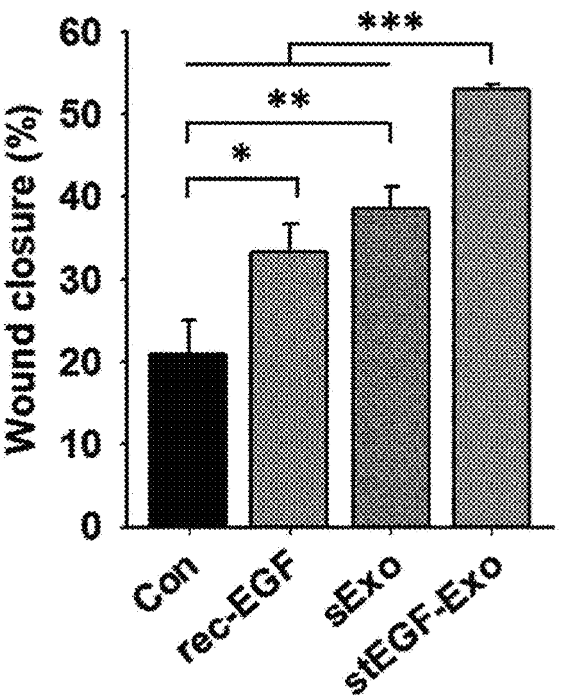
FIG. 7H represents a graph quantifying the results shown in FIG. 7G.

10 μg/ml of recombinant exosomes (stEGF-Exo), 10 μg/ml of control exosomes (sExo) isolated from non-transfected MSCs, and recombinant EGFs (rec-EGF) having the same molar concentration as EGFs existing in 10 μg/ml of stEGF-Exo were treated with Balb/3T3 cells with scratches induced. As shown in FIG. 7G and FIG. 7H, the wound healing effect of the recombinant exosomes (stEGF-Exo) was higher than that of the control exosomes (sExo) and that of the recombinant EGFs.

Experimental Example 6: Study of the Mechanism of Action of Recombinant Exosomes Having EGFs Displayed on Membrane Surface The reason why the wound healing effect of the recombinant exosomes comprising EGFs displayed on the surface membrane of exosomes was higher than that of free form EGFs was analyzed.

Figure 8:
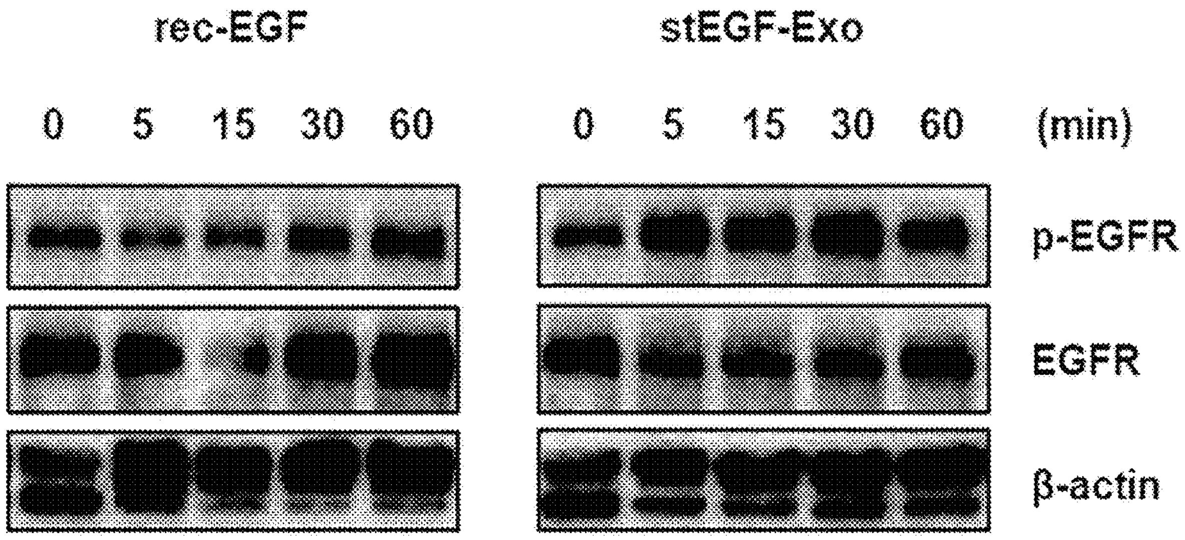
FIG. 8 is a Western Blot photograph showing the amounts of EGFR and phosphorylated EGFR measured over time in HaCaT human keranitocytes that are treated with the recombinant exosomes (stEGG-Exo, right) of embodiments of the present invention and with the free form recombinant EGF (rec-EGF, left) having the same molar concentration as the recombinant exosomes have.

To this end, 10 μg/ml of the recombinant exosomes (stEGF-Exo) and recombinant EGFs (rec-EGF, 1 ng/ml) having the same molar concentration as EGFs existing in 10 μg/ml of the recombinant exosomes were treated with HaCaT human keratinocytes, and the expression degree of EGFRs and phosphorylated EGFRs was analyzed over time by Western Blot analysis. As shown in FIG. 8, the recombinant exosomes (stEGF-Exo) according to embodiments of the present invention promoted EGFR phosphorylation more effectively than the recombinant EGFs (rec-EGF) did. This means that the recombinant exosomes (stEGF-Exo) induced EGFR signals more effectively than the free from recombinant EGFs (rec-EGF).

Experimental Example 7: Analysis of In Vivo Wound Healing Effect

From the experimental results of Experimental Examples 5 and 6, the in vivo wound healing effect of the recombinant exosomes (stEGF-Exo) obtained from MSCs transformed to express EGFs on the membrane surface was analyzed.

To this end, a wound model mouse was prepared as described below.

After anesthetizing a 7-week-old Balb/c mouse, the mouse was depilated with a hair removal cream. Then, with a sterile biopsy punch, a complete excision wound of 8 mm was made in the center of the back of the mouse.

Figure 9A:
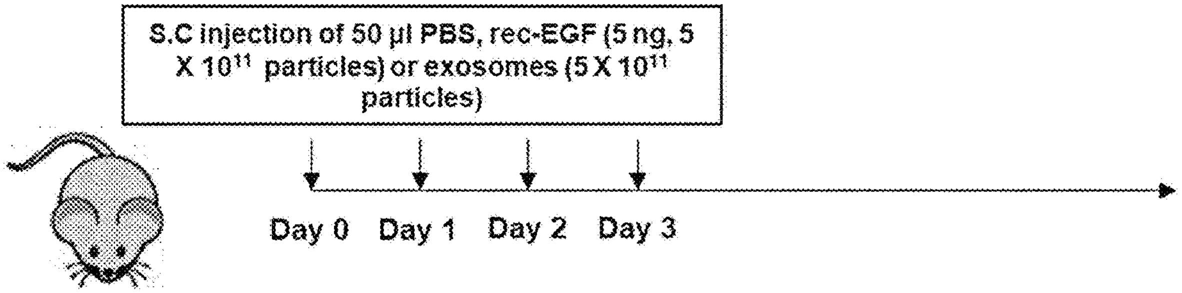
FIG. 9A is a schematic diagram illustrating an animal experiment schedule used for confirming the in vivo wound healing effect of recombinant exosomes according to embodiments of the present invention.

According to the administration schedule shown in FIG. 9A, PBS, recombinant EGFs (rec-EGF), and exosomes (sExo) isolated from non-transfected MSCs, as control groups, were administered to the wound model mouse, and the recombinant exosomes (stEGF-Exo) prepared in Example 4 were administered to the wound model mouse. More specifically, $5\times10^{11}$ of the recombinant exosomes were administered, and 5 ng of the recombinant EGFs, which is equivalent to the $5\times10^{11}$ recombinant exosomes were administered.

Figure 9B:
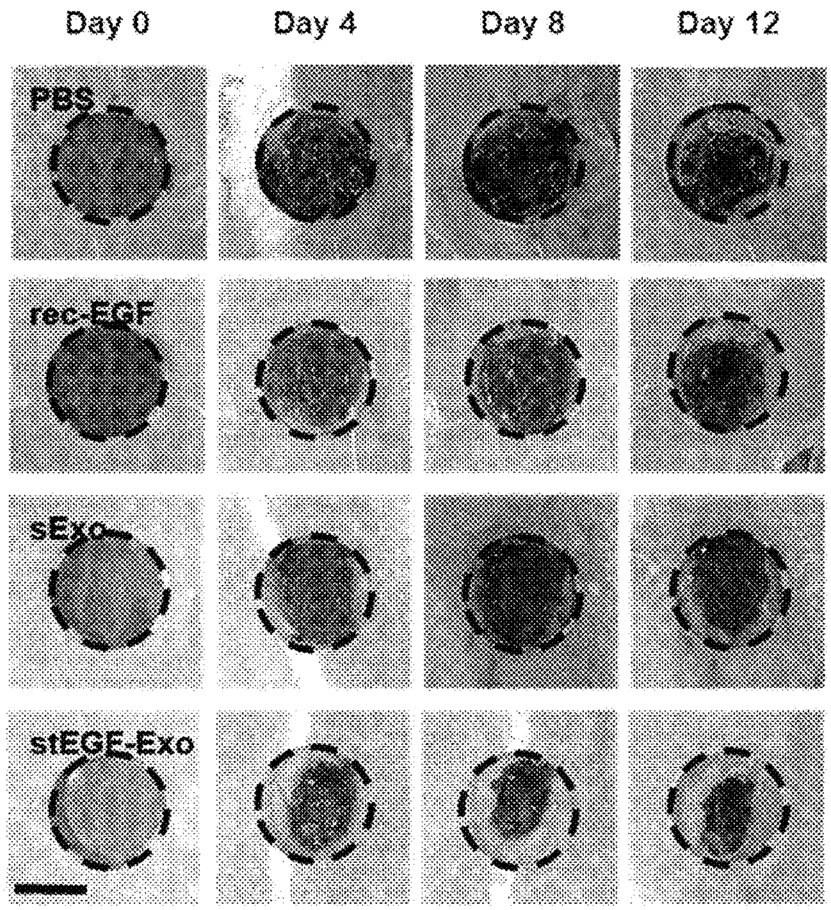
FIG. 9B represents photographs showing the degree of wound recovery that the free form EGF (rec-EGF), the control exosomes (sExo), and the recombinant exosomes (stEGF-Exo), respectively, exhibit when they are subcutaneously administered, respectively, according to the experimental schedule of FIG. 9A.
Figure 9C:
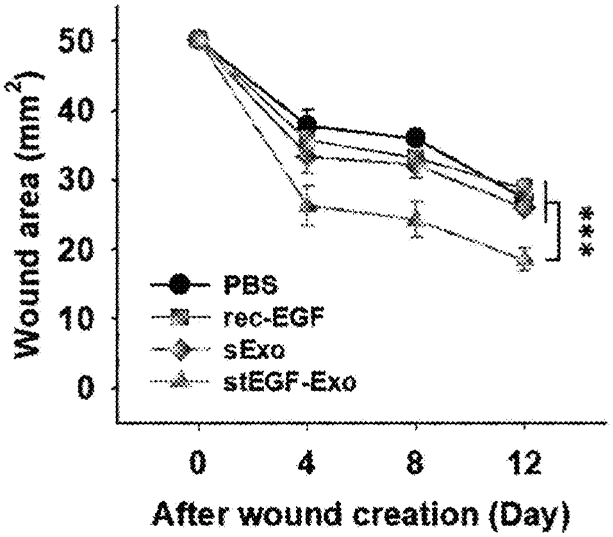
FIG. 9C is a graph quantifying the results shown in FIG. 9B.

As shown in FIGS. 9B and 9C, the wound healing effect of the stEGF-Exo was excellent. On the other hand, the wound healing effect of the recombinant EGFs (rec-EGF) and that of the control exosomes (sExo) were slightly higher than that of the negative control, but the difference was not statistically significant.

These results suggest that the recombinant exosomes according to embodiments of the present invention exhibited a significantly remarkable wound healing effect that cannot be expected from the free form recombinant EGFs or the exosomes isolated from non-transfected stem cells.

Figure 9D:
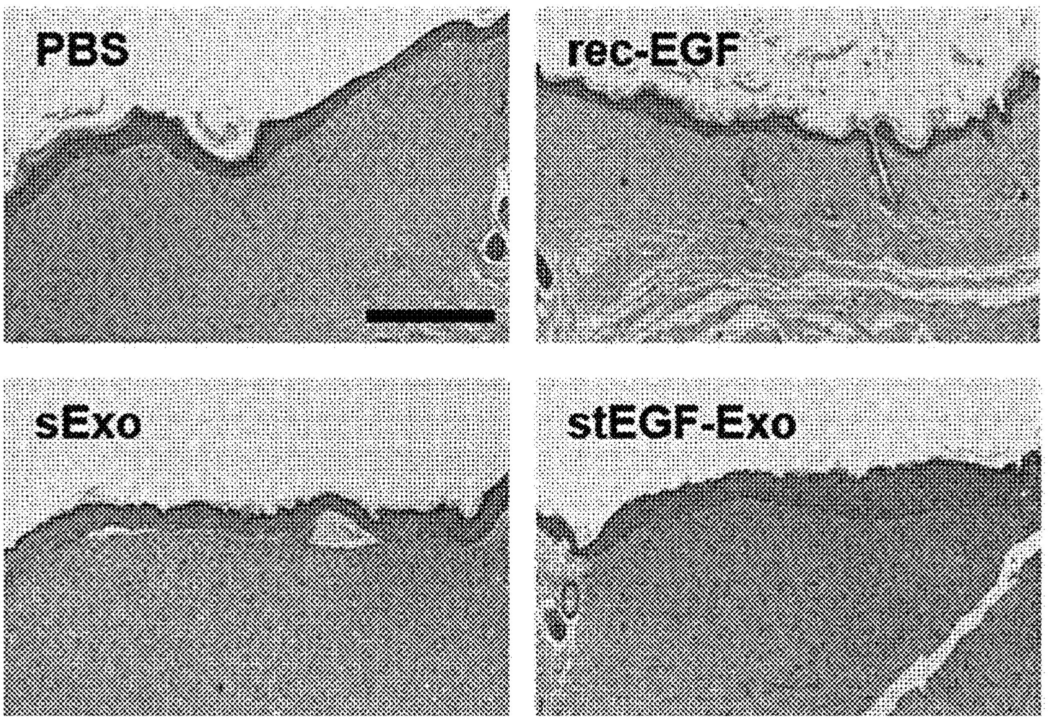
FIG. 9D represents microscopic photographs obtained by preparing tissue fragments through extracting wound sites from the test mouse on the 12th day of the experiment and subjecting the tissue fragments to hematoxillin and eosin staining.
Figure 9E:
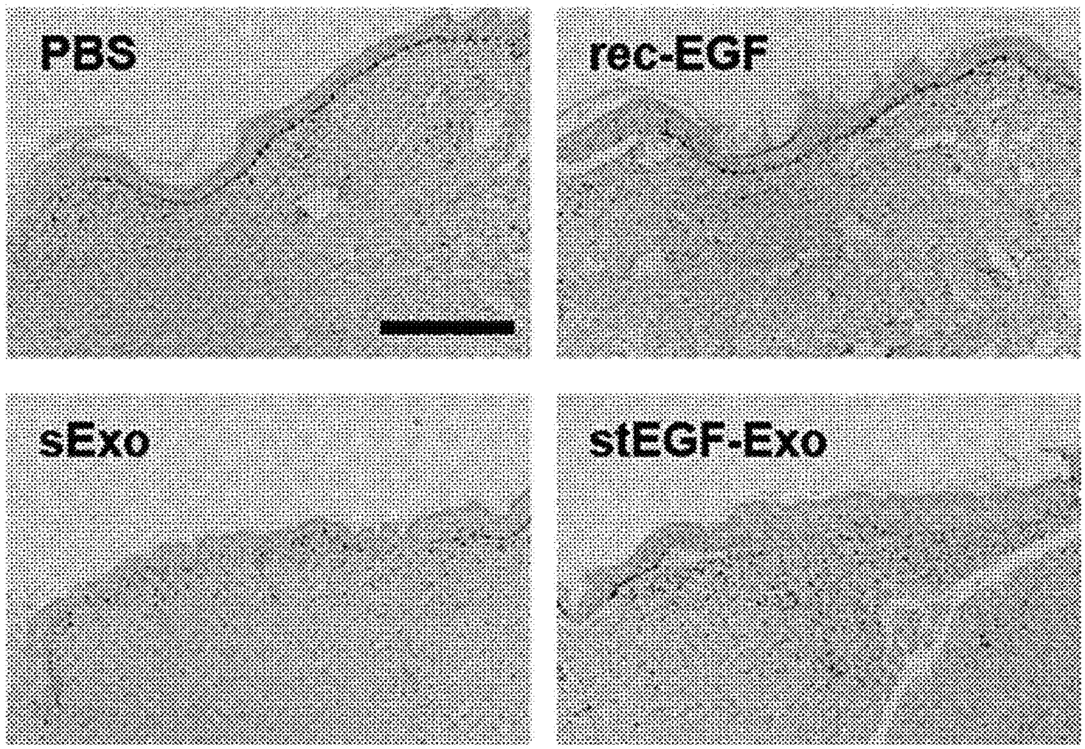
FIG. 9E represents microscopic photographs obtained by preparing tissue fragments through extracting wound sites from the test mouse on the 12th day of the experiment and subjecting the tissue fragments to immunohistochemical analysis using an anti-Ki67 antibody.

In addition, the degree of the wound healing effect was also analyzed by extracting the wound sites on the 12th day of the experiment from the mouse used to analyze the above-described in vivo wound healing effect and subjecting it to hematoxillin and eosin staining (FIG. 9D) and immunohistochemical analysis using Ki67 protein (FIG. 9E).

As shown in FIG. 9D, the recombinant exosomes (stEGF-Exo) healed wounds faster, and as shown in FIG. 9E, a higher amount of $Ki67^{+}$ cells, which are factors related to cell proliferation, existed the stEGF-Exo treatment group. This means that the recombinant exosomes (stEGF-Exo) healed wounds in vivo effectively through cell proliferation.

Preparation Example 1: Nourishing Lotion

A nourishing lotion containing exosomes derived from commercially available milk or colostrum was prepared by combining the ingredients by the composition ratio Table 1 below, according to an embodiment of the present invention.

TABLE 1

Composition ratio of nourishing lotion

| Ingredients | Content (unit: wt %) |
|---|---|
| Recombinant exosomes of Example 1 or 2 | 0.5 |
| Glyceryl Stearate SE | 1.5 |
| Cetearyl alcohol | 1.5 |
| Lanolin | 1.5 |
| Polysorbate 60 | 1.3 |
| Sorbitan stearate | 0.5 |
| Hydrogenated palm oil | 4.0 |
| Mineral oil | 5.0 |
| Trioctanoin | 2.0 |
| Dimethicone | 0.8 |
| Tocopherol acetate | 0.5 |
| Carboxyvinyl polymer | 0.12 |

TABLE 1-continued

Composition ratio of nourishing lotion

| Ingredients | Content (unit: wt %) |
|---|---|
| Glycerin | 5.0 |
| 1,3-Butylene glycol | 3.0 |
| Sodium hyaluronate | 5.0 |
| Triethanolapine | 0.12 |
| Uniside U-13 | 0.02 |
| Distilled water | remaining |
| Sum | 100 |

Preparation Example 2: Nourishing Cream

A nourishing cream containing exosomes derived from commercially available milk or colostrum was prepared by combining the ingredients by the composition ratio Table 2 below, according to an embodiment of the present invention.

TABLE 2

Composition ratio of nourishing cream

| ingredient | Content (unit: wt %) |
|---|---|
| Recombinant exosomes of Example 1 or 2 | 0.5 |
| Hydrophobic glycerin monosterarate | 1.5 |
| Cetearyl alcohol | 1.5 |
| Stearic acid | 1.0 |
| Polysorbate 60 | 1.5 |
| Sorbitan stearate | 0.6 |
| Isostearyl isosterate | 5.0 |
| Squalene | 5.0 |
| Mineral oil | 35.0 |
| Dimethicone | 0.5 |
| Hydroxyethylcellulose | 0.12 |
| Triethanolamine | 0.7 |
| Glycerin | 5.0 |
| Uniside U-13 | 0.02 |
| Distilled water | Remaining |
| Sum | 100 |

The recombinant exosomes according to embodiments of the present invention, although they were treated at significantly low concentrations, showed higher cell proliferation effects than recombinant EGFs did. Moreover, while existing recombinant EGFs have stability problems, the recombinant exosomes are expected to have less stability problems as the EGFs exist on the surface of the recombinant exosomes, which will allow the recombinant exosomes, even in the form of a topical agent, to be used to efficiently regenerate skin cells and treat wounds. Therefore, the recombinant exosomes according to embodiments of the present invention can be useful as a raw material to be used to make agents for treating wounds or various ulcers to make functional cosmetics for regenerating skins.

The present invention has been described with reference to the above-described embodiments, experimental examples, and preparation examples, but these are only exemplary, and those skilled in the art will understand that various modifications and uniform other embodiments are possible therefrom. Therefore, the true scope of technical protection of the present invention should be determined by the technical spirit of the appended claims.

The recombinant exosomes according to embodiments of the present invention can be used to prepare functional cosmetic compositions for improving wrinkles as well as to prepare pharmaceutical compositions for treating wounds.

The invention claimed is:

1. A recombinant exosome comprising a membrane-bound epidermal growth factor (EGF) protein on the surface of the recombinant exosome, wherein the membrane-bound EGF protein is selected from the group consisting of:

(i) a full-length EGF protein comprising a PrePro peptide, a mature EGF, a transmembrane domain, and a cytoplasmic domain;

(ii) a fusion protein in which a mature EGF protein is directly linked to a transmembrane domain or is fixed to the membrane by a glycosylphosphatidylinositol (GPI) anchor; and (iii) a truncated EGF protein derived from the full-length EGF protein, wherein a protein cleavage site has been removed from the full-length EGF protein.

2. The recombinant exosome of claim 1, wherein the membrane-bound EGF protein further comprises a cytoplasmic domain derived from the membrane protein.

3. The recombinant exosome of claim 1, wherein the transmembrane domain is derived from a membrane protein other than epidermal growth factor receptor (EGFR).

4. The recombinant exosome of claim 3, wherein the transmembrane protein is a receptor protein, an ion channel, a transporter, a cluster of differentiation (CD), or a membrane-bound enzyme.

5. The recombinant exosome of claim 4, wherein the CD is CD28, CD38, CD45, CD4, CD5, CD8, CD9, CD16, CD22, CD33, CD37, CD64, CD80, CD86, CD134, CD137, or CD154.

6. The recombinant exosome of claim 4, wherein the receptor protein is a receptor tyrosine kinase (RTK), an immune receptor, or a G protein-coupling receptor (GPCR).

7. The recombinant exosome of claim 6, wherein the RTK is a platelet-derived growth factor receptor (PDGFR), a fibroblast growth factor receptor (FGFR), a vascular endothelial growth factor receptor (VEGFR), a hepatocyte growth factor receptor (HGFR), tropomyosin receptor kinase (Trk), an insulin receptor (IR), a Leukocyte receptor tyrosine kinase (LTK), an angiopoietin receptor, a receptor tyrosine kinase-like orphan receptor (ROR), a discoidin domain receptor (DDR), a rearranged during transfection receptor (RETR), a tyrosine-protein kinase-like (PTK), a receptor tyrosine kinase-related molecule (RYK), or a muscle-specific kinase (MuSK).

8. The recombinant exosome of claim 6, wherein the GPCR is an alpha receptor, a beta receptor, a chemokine receptor, a dopamine receptor, a histamine receptor, an opioid receptor, a nociceptin receptor, a sphingosine-1-phosphate receptor, an opsin, or rhodopsinin.

9. The recombinant exosome of claim 6, wherein the immune receptor is a pattern recognition receptor (PRR), a killer activated receptor (TAR), a killer inhibitor receptor (KIR), a complement receptor, an Fc receptor, a B cell receptor, a T cell receptor, or a cytokine receptor.

10. The recombinant exosome of claim 1, wherein the recombinant exosome is derived from a cell transfected with a nucleic acid encoding the membrane-bound EGF protein.

11. The recombinant exosome of claim 10, wherein the cell is CHO, HKB11, BHK21, HeLa, HEK293, HT-1080, PER.C6, or F2N78.

12. A pharmaceutical composition comprising the recombinant exosome of claim 1 as an active ingredient.

13. A method of treating wound or ulcer, which comprises administering a therapeutically effective amount of the recombinant exosome of claim 1 to a subject having wound or ulcer.

14. The method of claim 13, wherein the ulcer is a gastric ulcer, a lower limb ulcer, a skin ulcer, a genital ulcer, a mouth ulcer, an esophageal ulcer, a bladder ulcer, a gallbladder ulcer, a foot ulcer, duodenal ulcer, or a colon ulcer.

15. A method for proliferating epithelial cells, which comprises administering a therapeutically effective amount of the recombinant exosome of claim 1 to a subject having a symptom that requires proliferating epithelial cells.

16. The method of claim 15, wherein the symptom is selected from the group consisting of wound, burn, scar, keloid skin, eczema, psoriasis, acne, ulcers, dermatitis, rosacea, and atopic diseases.

17. A method of treating diabetic foot lesions (DM foot), which comprises administering a therapeutically effective amount of the recombinant exosome of claim 1 to a subject having DM foot.

18. A method of regenerating skin, alleviating skin aging, or improving wrinkles, which comprises administering a therapeutically effective amount of the recombinant exosome of claim 1 to a subject in need of skin regeneration, skin aging relief, or wrinkle improvement.

* * * * *

SEQUENCE LISTING

```
Sequence total quantity: 6
SEQ ID NO: 1           moltype = AA  length = 1207
FEATURE                Location/Qualifiers
source                 1..1207
                       mol_type = protein
                       organism = Homo sapiens
SEQUENCE: 1
MLLTLIILLP VVSKFSFVSL SAPQHWSCPE GTLAGNGNST CVGPAPFLIF SHGNSIFRID  60
TEGTNYEQLV VDAGVSVIMD FHYNEKRIYW VDLERQLLQR VFLNGSRQER VCNIEKNVSG  120
MAINWINEEV IWSNQQEGII TVTDMKGNNS HILLSALKYP ANVAVDPVER FIFWSSEVAG  180
SLYRADLDGV GVKALLETSE KITAVSLDVL DKRLFWIQYN REGSNSLICS CDYDGGSVHI  240
SKHPTQHNLF AMSLFGDRIF YSTWKMKTIW IANKHTGKDM VRINLHSSFV PLGELKVVHP  300
LAQPKAEDDT WEPEQKLCKL RKGNCSSTVC GQDLQSHLCM CAEGYALSRD RKYCEDVNEC  360
AFWNHGCTLG CKNTPGSYYC TCPVGFVLLP DGKRCHQLVS CPRNVSECSH DCVLTSEGPL  420
CFCPEGSVLE RDGKTCSGCS SPDNGGCSQL CVPLSPVSWE CDCFPGYDLQ LDEKSCAASG  480
PQPFLLFANS QDIRHMHFDG TDYGTLLSQQ MGMVYALDHD PVENKIYFAH TALKWIERAN  540
MDGSQRERLI EEGVDVPEGL AVDWIGRRFY WTDRGKSLIG RSDLNGKRSK IITKENISQP  600
RGIAVHPMAK RLFWTDTGIN PRIESSSLQG LGRLVIASSD LIWPSGITID FLTDKLYWCD  660
AKQSVIEMAN LDGSKRRRLT QNDVGHPFAV AVFEDYVWFS DWAMPSVMRV NKRTGKDRVR  720
LQGSMLKPSS LVVVHPLAKP GADPCLYQNG GCEHICKKRL GTAWCSCREG FMKASDGKTC  780
LALDGHQLLA GGEVDLKNQV TPLDILSKTR VSEDNITESQ HMLVAEIMVS DQDDCAPVGC  840
SMYARCISEG EDATCQCLKG FAGDGKLCSD IDECEMGVPV CPPASSKCIN TEGGYVCRCS  900
EGYQGDGIHC LDIDECQLGE HSCGENASCT NTEGGYTCMC AGRLSEPGLI CPDSTPPPHL  960
REDDHHYSVR NSDSECPLSH DGYCLHDGVC MYIEALDKYA CNCVVGYIGE RCQYRDLKWW  1020
ELRHAGHGQQ QKVIVVAVCV VVLVMLLLLS LWGAHYYRTQ KLLSKNPKNP YEESSRDVRS  1080
RRPADTEDGM SSCPQPWFVV IKEHQDLKNG GQPVAGEDGQ AADGSMQPTS WRQEPQLCGM  1140
GTEQGCWIPV SSDKGSCPQV MERSFHMPSY GTQTLEGGVE KPHSLLSANP LWQQRALDPP  1200
HQMELTQ                                                           1207

SEQ ID NO: 2           moltype = DNA  length = 3624
FEATURE                Location/Qualifiers
source                 1..3624
                       mol_type = genomic DNA
                       organism = Homo sapiens
SEQUENCE: 2
atgctgctca ctcttatcat tctgttgcca gtagtttcaa aatttagttt tgttagtctc  60
tcagcaccgc agcactggag ctgtcctgaa ggtactctcg caggaaatgg gaattctact  120
tgtgtgggtc ctgcaccctt cttaattttc tcccatggaa atagtatctt taggattgac  180
acagaaggaa ccaattatga gcaattggtg gtggatgctg gtgtctcagt gatcatggat  240
tttcattata atgagaaaag aatctattgg gtggatttag aaagacaact tttgcaaaga  300
gtttttctga atgggtcaag gcaagagaga gtatgtaata tagagaaaaa tgtttctgga  360
atggcaataa attggataaa tgaagaagtt atttggtcaa atcaacagga aggaatcatt  420
acagtaacag atatgaaagg aaataattcc cacattcttt taagtgcttt aaaatatcct  480
gcaaatgtag cagttgatcc agtagaaagg tttatatttt ggtcttcaga ggtggctgga  540
agcctttata gagcagatct cgatggtgtg ggagtgaagg ctctgttgga gacatcagag  600
aaaataacag ctgtgtcatt ggatgtgctt gataagcggc tgttttggat tcagtacaac  660
agagaaggaa gcaattctct tatttgctcc tgtgattatg atggaggttc tgtccacatt  720
agtaaacatc caacacagca taatttgttt gcaatgtccc tttttggtga ccgtatcttc  780
tattcaacat ggaaaatgaa gacaatttgg atagccaaca aacacactgg aaaggacatg  840
gttagaatta acctccattc atcatttgta ccacttggtg aactgaaagt agtgcatcca  900
cttgcacaac ccaaggcaga agatgacact tgggagcctg agcagaaact ttgcaaattg  960
aggaaaggaa actgcagcag cactgtgtgt gggcaagacc tccagtcaca cttgtgcatg  1020
tgtgcagagg gatacgccct aagtcgagac cggaagtact gtgaagatgt taatgaatgt  1080
gctttttgga atcatggctg tactcttggg tgtaaaaaca cccctggatc ctattactgc  1140
acgtgccctg taggatttgt tctgcttcct gatgggaaac gatgtcatca acttgtttcc  1200
tgtccacgca atgtgtctga atgcagccat gactgtgttc tgacatcaga aggtccctta  1260
tgtttctgtc ctgaaggctc agtgcttgag agagatggga aaacatgtag cggttgttcc  1320
tcacccgata atggtggatg tagccagctc tgcgttcctc ttagcccagt atcctgggaa  1380
tgtgattgct ttcctgggta tgacctacaa ctggatgaaa aaagctgtgc agcttcagga  1440
ccacaaccat tttgctgtt tgccaattct caagatattc gacacatgca ttttgatgga  1500
acagactatg gaactctgct cagccagcag atgggaatgg tttatgccct agatcatgac  1560
cctgtggaaa ataagatata ctttgcccat acagccctga agtggataga gagagctaat  1620
atggatggtt cccagcgaga aaggcttatt gaggaaggag tagatgtgcc agaaggtctt  1680
gctgtggact ggattggccg tagattctat tggacagaca gagggaaatc tctgattgga  1740
aggagtgatt taaatgggaa acgttccaaa ataatcacta aggagaacat ctctcaacca  1800
cgaggaattg ctgttcatcc aatggccaag agattattct ggactgatac agggattaat  1860
ccacgaattg aaagttcttc cctccaaggc cttggccgtc tggttatagc cagctctgat  1920
ctaatctggc ccagtggaat aacgattgac ttcttaactg acaagttgta ctggtgcgat  1980
gccaagcagt ctgtgattga aatggccaat ctggatggtt caaaacgccg aagacttacc  2040
cagaatgatg taggtcaccc atttgctgta gcagtgtttg aggattatgt gtggttctca  2100
gattgggcta tgccatcagt aataagagta aacaagagga ctggcaaaga tagagtacgt  2160
ctccaaggca gcatgctgaa gccctcatca ctggttgtgg ttcatccatt ggcaaaacca  2220
ggagcagatc cctgcttata tcaaaacgga ggctgtgaac atatttgcaa aaagaggctt  2280
ggaactgctt ggtgttcgtg tcgtgaaggt tttatgaaag cctcagatgg gaaaacgtgt  2340
ctggctctgg atggtcatca gctgttggca ggtggtgaag ttgatctaaa gaaccaagta  2400
acaccattgg acatcttgtc caagactaga gtgtcagaag ataacattac agaatctcaa  2460
cacatgctag tggctgaaat catggtgtca gatcaagatg actgtgctcc tgtgggatgc  2520
agcatgtatg ctcggtgtat ttcagaggga gaggatgcca catgtcagtg tttgaaagga  2580
```

-continued

```
tttgctgggg atggaaaact atgttctgat atagatgaat gtgagatggg tgtcccagtg  2640
tgcccccctg cctcctccaa gtgcatcaac accgaaggtg gttatgtctg ccggtgctca  2700
gaaggctacc aaggagatgg gattcactgt cttgatattg atgagtgcca actgggggtg  2760
cacagctgtg gagagaatgc cagctgcaca aatacagagg gaggctatac ctgcatgtgt  2820
gctggacgcc tgtctgaacc aggactgatt tgccctgact ctactccacc ccctcacctc  2880
agggaagatg accaccacta ttccgtaaga aatagtgact ctgaatgtcc cctgtcccac  2940
gatgggtact gcctccatga tggtgtgtgc atgtatattg aagcattgga caagtatgca  3000
tgcaactgtg ttgttggcta catcggggag cgatgtcagt accgagacct gaagtggtgg  3060
gaactgcgcc acgctggcca cgggcagcag cagaaggtca tcgtggtggc tgtctgcgtg  3120
gtggtgcttg tcatgctgct cctcctgagc ctgtgggggg cccactacta caggactcag  3180
aagctgctat cgaaaaaccc aaagaatcct tatgaggagt cgagcagaga tgtgaggagt  3240
cgcaggcctg ctgacactga ggatgggatg tcctcttgcc ctcaaccttg gtttgtggtt  3300
ataaaagaac accaagacct caagaatggg ggtcaaccag tggctggtga ggatggccag  3360
gcagcagatg ggtcaatgca accaacttca tggaggcagg agccccagtt atgtggaatg  3420
ggcacagagc aaggctgctg gattccagta tccagtgata agggctcctg tccccaggta  3480
atggagcgaa gctttcatat gccctcctat gggacacaga cccttgaagg gggtgtcgag  3540
aagccccatt ctctcctatc agctaaccca ttatggcaac aaagggccct ggacccacca  3600
caccaaatgg agctgactca gtga                                          3624

SEQ ID NO: 3            moltype = AA  length = 53
FEATURE                 Location/Qualifiers
REGION                  1..53
                        note = mature EGF
source                  1..53
                        mol_type = protein
                        organism = synthetic construct
SEQUENCE: 3
NSDSECPLSH DGYCLHDGVC MYIEALDKYA CNCVVGYIGE RCQYRDLKWW ELR        53

SEQ ID NO: 4            moltype = DNA  length = 159
FEATURE                 Location/Qualifiers
misc_feature            1..159
                        note = polynucleotide encoding mature EGF
source                  1..159
                        mol_type = other DNA
                        organism = synthetic construct
SEQUENCE: 4
aatagtgact ctgaatgtcc cctgtcccac gatgggtact gcctccatga tggtgtgtgc  60
atgtatattg aagcattgga caagtatgca tgcaactgtg ttgttggcta catcggggag  120
cgatgtcagt accgagacct gaagtggtgg gaactgcgc                         159

SEQ ID NO: 5            moltype = AA  length = 250
FEATURE                 Location/Qualifiers
REGION                  1..250
                        note = truncated EGF
source                  1..250
                        mol_type = protein
                        organism = synthetic construct
SEQUENCE: 5
MLLTLIILLP VVSKFSFVSL SANSDSECPL SHDGYCLHDG VCMYIEALDK YACNCVVGYI  60
GERCQYRDLK WWELRVIVVA VCVVVLVMLL LLSLWGAHYY RTQKLLSKNP KNPYEESSRD  120
VRSRRPADTE DGMSSCPQPW FVVIKEHQDL KNGGQPVAGE DGQAADGSMQ PTSWRQEPQL  180
CGMGTEQGCW IPVSSDKGSC PQVMERSFHM PSYGTQTLEG GVEKPHSLLS ANPLWQQRAL  240
DPPHQMELTQ                                                         250

SEQ ID NO: 6            moltype = DNA  length = 750
FEATURE                 Location/Qualifiers
misc_feature            1..750
                        note = polynucleotide encoding truncated EGF
source                  1..750
                        mol_type = other DNA
                        organism = synthetic construct
SEQUENCE: 6
atgctgctca ctcttatcat tctgttgcca gtagtttcaa aatttagttt tgttagtctc  60
tcagcaaata gtgactctga atgtcccctg tcccacgatg ggtactgcct ccatgatggt  120
gtgtgcatgt atattgaagc attggacaag tatgcatgca actgtgttgt tggctacatc  180
ggggagcgat gtcagtaccg agacctgaag tggtgggaac tgcgcgtcat cgtggtggct  240
gtctgcgtgg tggtgcttgt catgctgctc ctcctgagcc tgtggggggc ccactactac  300
aggactcaga agctgctatc gaaaaaccca aagaatcctt atgaggagtc gagcagagat  360
gtgaggagtc gcaggcctgc tgacactgag gatgggatgt cctcttgccc tcaaccttgg  420
tttgtggtta taaaagaaca ccaagacctc aagaatgggg gtcaaccagt ggctggtgag  480
gatggccagg cagcagatgg gtcaatgcaa ccaacttcat ggaggcagga gccccagtta  540
tgtggaatgg gcacagagca aggctgctgg attccagtat ccagtgataa gggctcctgt  600
ccccaggtaa tggagcgaag ctttcatatg ccctcctatg ggacacagac ccttgaaggg  660
ggtgtcgaga agccccattc tctcctatca gctaacccat tatggcaaca aagggccctg  720
gacccaccac accaaatgga gctgactcag                                  750
```